(12) United States Patent
Griffin et al.

(10) Patent No.: US 8,492,429 B2
(45) Date of Patent: Jul. 23, 2013

(54) COMBINATION OF IAP INHIBITORS AND FLT3 INHIBITORS

(75) Inventors: James Douglas Griffin, Brookline, MA (US); Leigh Zawel, Hingham, MA (US)

(73) Assignee: Novartis AG, Basel (CH)

( * ) Notice: Subject to any disclaimer, the term of this patent is extended or adjusted under 35 U.S.C. 154(b) by 385 days.

(21) Appl. No.: 12/516,062

(22) PCT Filed: Nov. 27, 2007

(86) PCT No.: PCT/US2007/085579
§ 371 (c)(1),
(2), (4) Date: May 22, 2009

(87) PCT Pub. No.: WO2008/067280
PCT Pub. Date: Jun. 5, 2008

(65) Prior Publication Data
US 2010/0056467 A1    Mar. 4, 2010

Related U.S. Application Data

(60) Provisional application No. 60/867,448, filed on Nov. 28, 2006, provisional application No. 60/891,088, filed on Feb. 22, 2007.

(51) Int. Cl.
*A61K 31/40* (2006.01)
*A01N 43/38* (2006.01)

(52) U.S. Cl.
USPC .......................................... 514/422; 514/410

(58) Field of Classification Search
None
See application file for complete search history.

(56) References Cited

FOREIGN PATENT DOCUMENTS

| WO | WO 2004/005248 | | 1/2004 |
|---|---|---|---|
| WO | 2005/097791 | | 10/2005 |
| WO | WO 2005097791 | A1 * | 10/2005 |
| WO | 2007/075525 | | 7/2007 |
| WO | 2008-016893 | | 2/2008 |
| WO | WO 2008016893 | A1 * | 2/2008 |

OTHER PUBLICATIONS

Weisberg, E et al., Smac mimetics: implications for enhancement of targeted therapies in leukemia, Leukemia. Dec. 2010;24(12):2100-9.*
Office Communication sent and received electronically on Jan. 19, 2012 for U.S. Appl. No. 13/178,946.

* cited by examiner

*Primary Examiner* — Sreeni Padmanabhan
*Assistant Examiner* — Svetlana M Ivanova
(74) *Attorney, Agent, or Firm* — George Dohmann

(57) ABSTRACT

The present invention relates to methods of treating hematological malignancies, including acute myeloid leukemia (AML), comprising the combination of a compound that inhibits the binding of the Smac protein to IAPs ("IAP inhibitor") and one or more pharmaceutically active agents; pharmaceutical compositions comprising said combination; and a commercial package comprising said combination. The present invention also relates to the use of IAP inhibitors in combination with one or more pharmaceutically active agents for the preparation of a medicament to treat hematological malignancies, including AML.

6 Claims, 16 Drawing Sheets

FIG 1
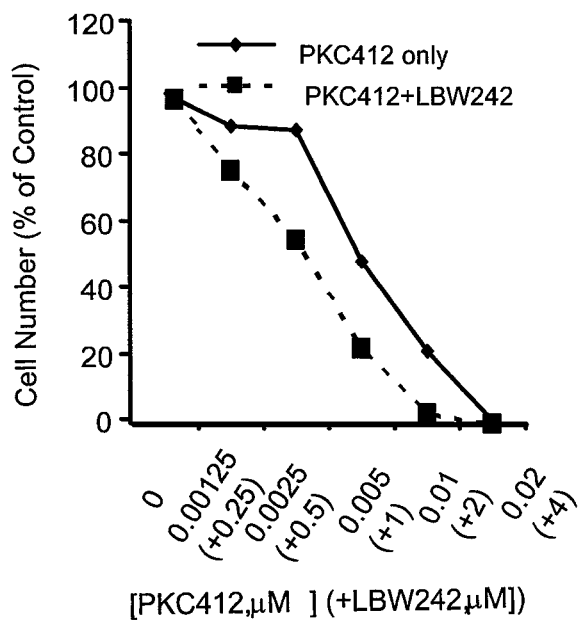
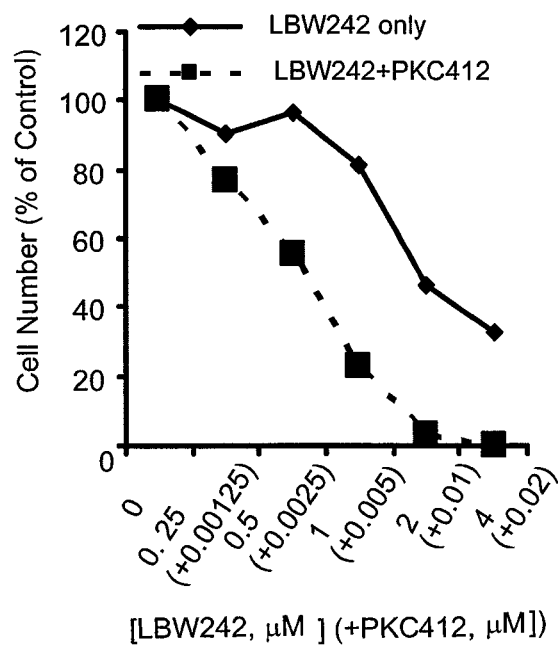

FIG 2
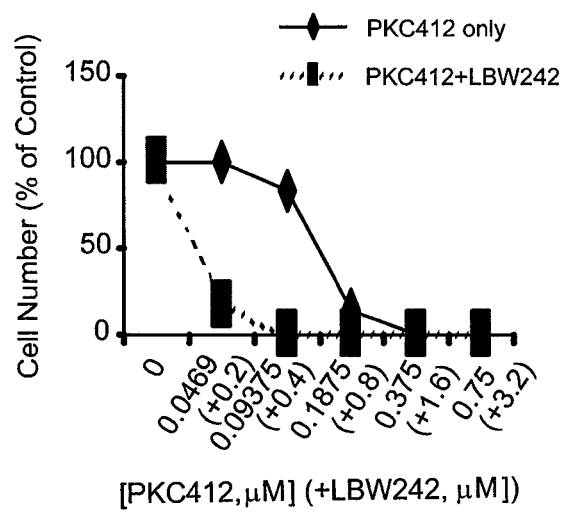
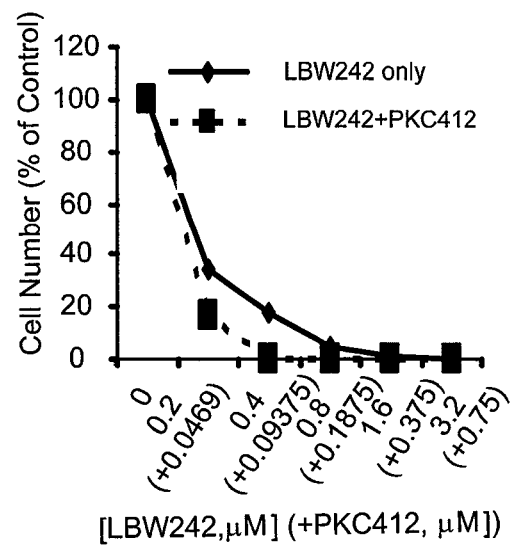

FIG 3
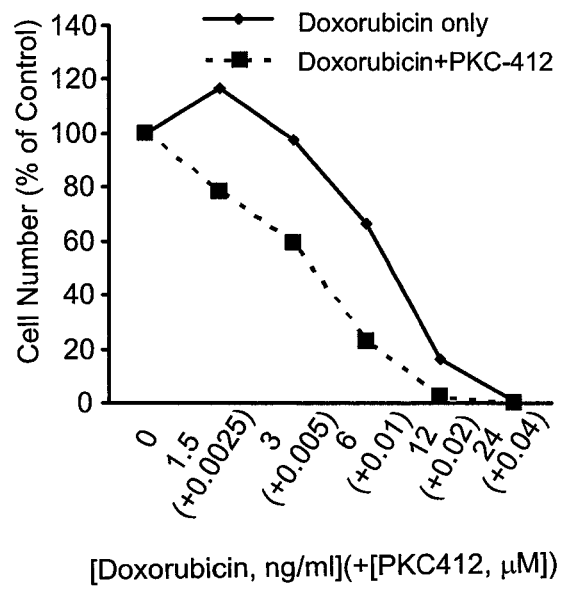
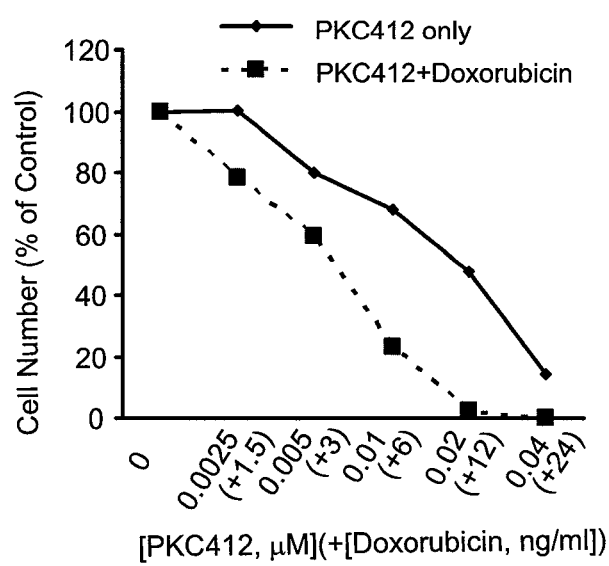

FIG 4
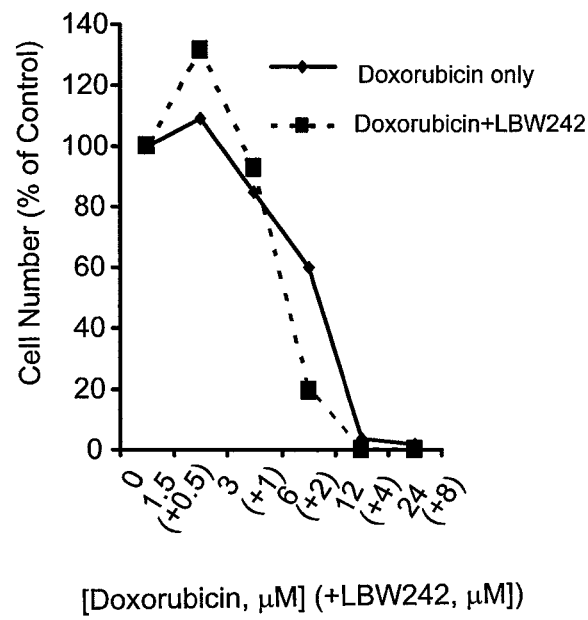
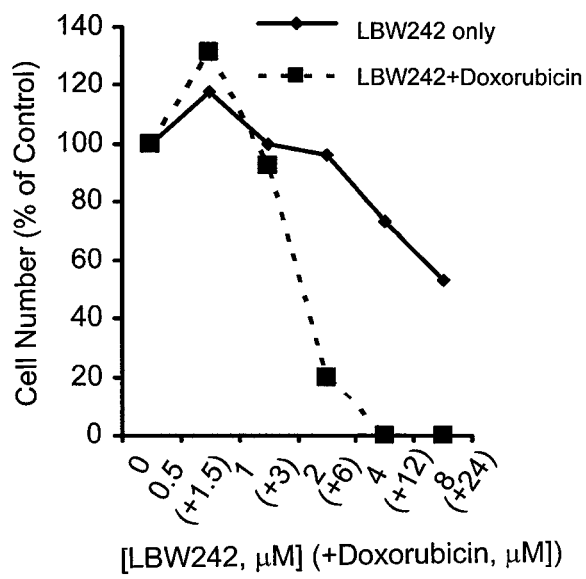

FIG 5
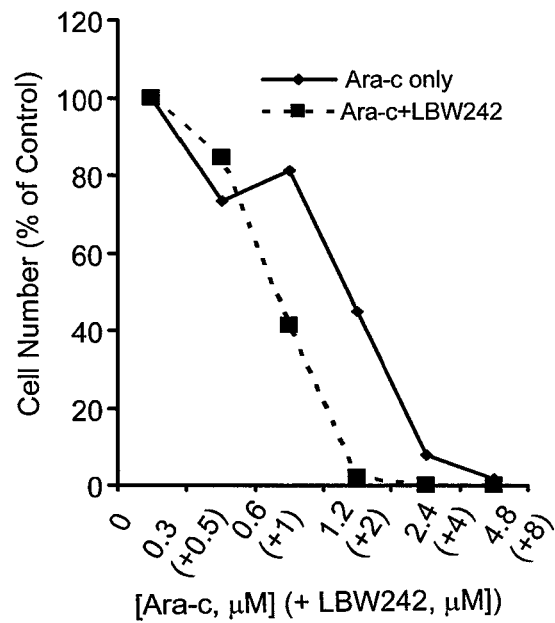
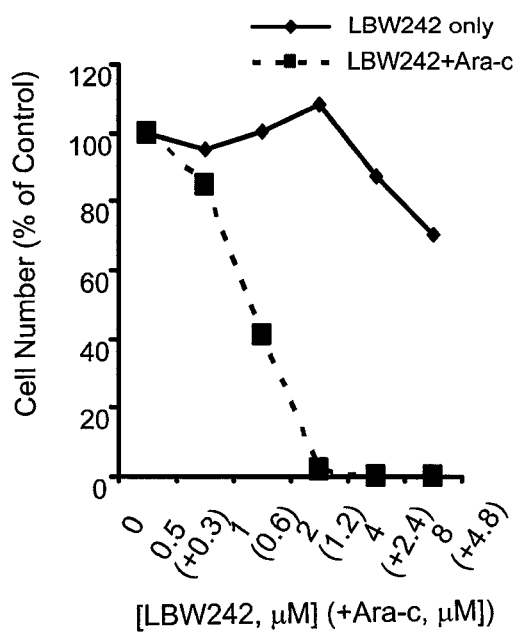

FIG 9
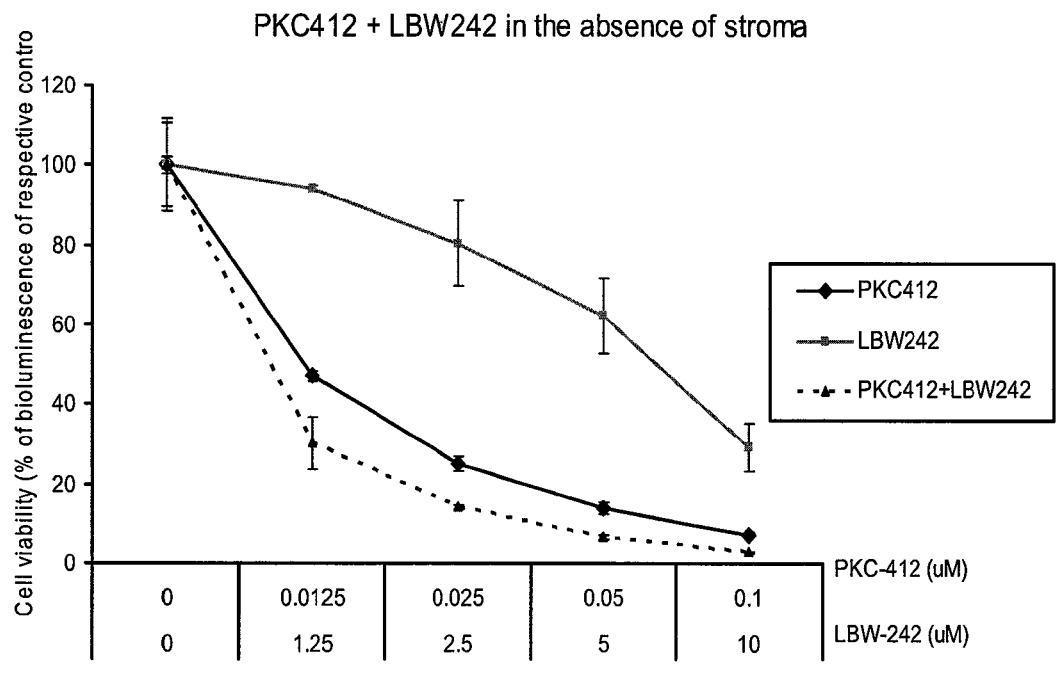
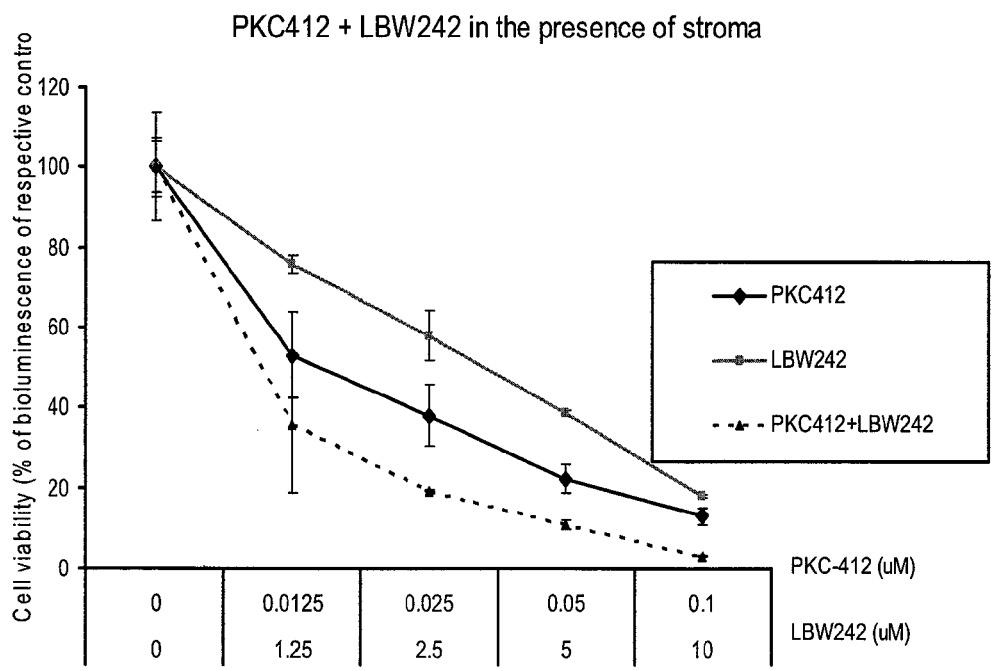

COMBINATION OF IAP INHIBITORS AND FLT3 INHIBITORS

This is a National Stage of International Application No. PCT/US2007/085579 filed Nov. 27, 2007, which claims benefit of U.S. Provisional Application No. 60/867,448 filed Nov. 28, 2006 and U.S. Provisional Application No. 60/891,088 filed Feb. 22, 2007, which in their entirety are herein incorporated by reference.

The present invention, as defined by the claims herein, was made by parties to a Joint Research Agreement ("Agreement") between Novartis and Dana Farber Cancer Institute, as a result of activities undertaken within the scope of that Agreement. The Agreement was in effect prior to the date of the invention.

The present invention relates to combinations of IAP inhibitors and FLT3 inhibitors, pharmacological compositions comprising said combination, methods of treating hematological malignancies, including acute myeloid leukemia (AML), comprising the combination of a compound that inhibits the binding of the second mitochondria-derived activator of caspase (Smac) protein to inhibitor of apoptosis (IAP inhibitor) and one or more pharmaceutically active agents and the use of these combinations for the treatment of acute myeloid leukemia; and a commercial package comprising said combination.

The present invention also relates to the use of IAP inhibitors in combination with one or more pharmaceutically active agents for the preparation of a medicament to treat hematological malignancies, including AML.

In one embodiment, the present invention also relates to the use of IAP inhibitors in combination with one or more FLT inhibitors for the preparation of a medicament to treat hematological malignancies, including AML.

BACKGROUND OF INVENTION

FLT3, is a promising therapeutic target for leukemia and is mutated in approximately ⅓ of AML patients. Of growing concern, however, is the development of drug resistance resulting from the emergence of point mutations in targeted tyrosine kinases used for the treatment of acute leukemia patients. See Shah et al. (2002) and Cools et al. (2003). One approach to overriding such resistance is to combine structurally unrelated inhibitors and/or inhibitors of different signaling pathways.

SUMMARY OF THE INVENTION

The present invention relates to methods of treating a warm-blooded animal, especially a human, having leukemia, in particular, AML, which is resistant to conventional chemotherapy, comprising administering to said animal a therapeutically effective amount of an IAP inhibitor; useful in AML treatment.

In another embodiment, the present invention relates to the use of IAP inhibitors in the preparation of a medicament for the treatment of hematological malignancies, including AML.

In one embodiment, the present invention also relates to the use of IAP inhibitors in combination with one or more FLT inhibitors for the preparation of a medicament to treat hematological malignancies, including AML.

DETAILED DESCRIPTION OF THE DRAWINGS

FIG. 1 illustrates proliferation study showing three-day treatments of FLT3-ITD-Ba/F3 cells with PKC412, N-[1-cyclohexyl-2-oxo-2-(6-phenethyl-octahydro-pyrrolo[2,3-c]pyridin-1-yl-ethyl]-2-methylamino-propionamide (LBW242) or a combination of PKC412 and N-[1-cyclohexyl-2-oxo-2-(6-phenethyl-octahydro-pyrrolo[2,3-c]pyridin-1-yl-ethyl]-2-methylamino-propionamide (LBW242).

FIG. 2 illustrates proliferation study showing three-day treatments of G697R-Ba/F3 cells with PKC412, N-[1-cyclohexyl-2-oxo-2-(6-phenethyl-octahydro-pyrrolo[2,3-c]pyridin-1-yl-ethyl]-2-methylamino-propionamide (LBW242) or a combination of PKC412 and N-[1-cyclohexyl-2-oxo-2-(6-phenethyl-octahydro-pyrrolo[2,3-c]pyridin-1-yl-ethyl]-2-methylamino-propionamide (LBW242).

FIG. 3 illustrates proliferation study showing three-day treatments of FLT3-ITD-Ba/F3 cells with PKC412, doxorubicin or a combination of PKC412 and doxorubicin.

FIG. 4 illustrates proliferation study showing three-day treatments of FLT3-ITD-Ba/F3 cells with doxorubicin, N-[1-cyclohexyl-2-oxo-2-(6-phenethyl-octahydro-pyrrolo[2,3-c]pyridin-1-yl-ethyl]-2-methylamino-propionamide (LBW242) or a combination of doxorubicin and N-[1-cyclohexyl-2-oxo-2-(6-phenethyl-octahydro-pyrrolo[2,3-c]pyridin-1-yl-ethyl]-2-methylamino-propionamide (LBW242) (n=1).

FIG. 5 illustrates proliferation study showing three-day treatments of FLT3-ITD-Ba/F3 cells with Ara-c, N-[1-cyclohexyl-2-oxo-2-(6-phenethyl-octahydro-pyrrolo[2,3-c]pyridin-1-yl-ethyl]-2-methylamino-propionamide (LBW242) or a combination of Ara-c and N-[1-cyclohexyl-2-oxo-2-(6-phenethyl-octahydro-pyrrolo[2,3-c]pyridin-1-yl-ethyl]-2-methylamino-propionamide (LBW242) (n=1).

FIG. 9 illustrates the treatment of MOLM13-luc+ cells with different concentrations of PKC412 in the absence and the presence of the human stromal cell line, HS-5.

Figure 11:
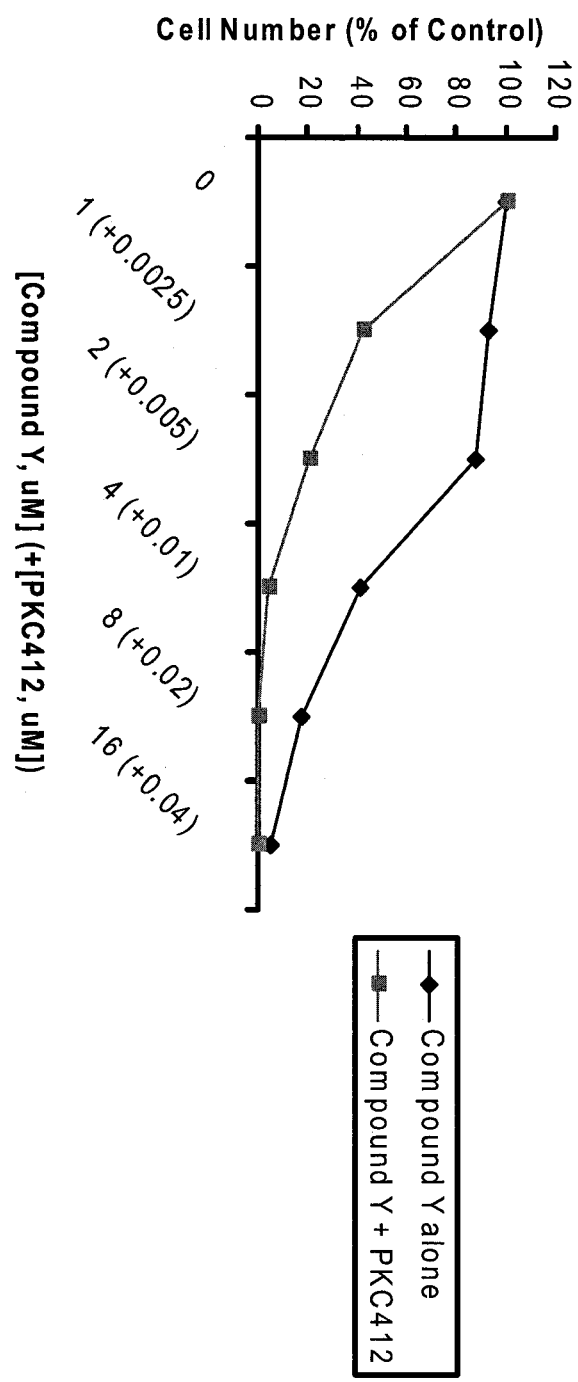

FIG. 11 illustrates proliferation study showing three-day treatments of MOLM13-luc+ cells with (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y), PKC412 or a combination of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and PKC412.

Figure 12:
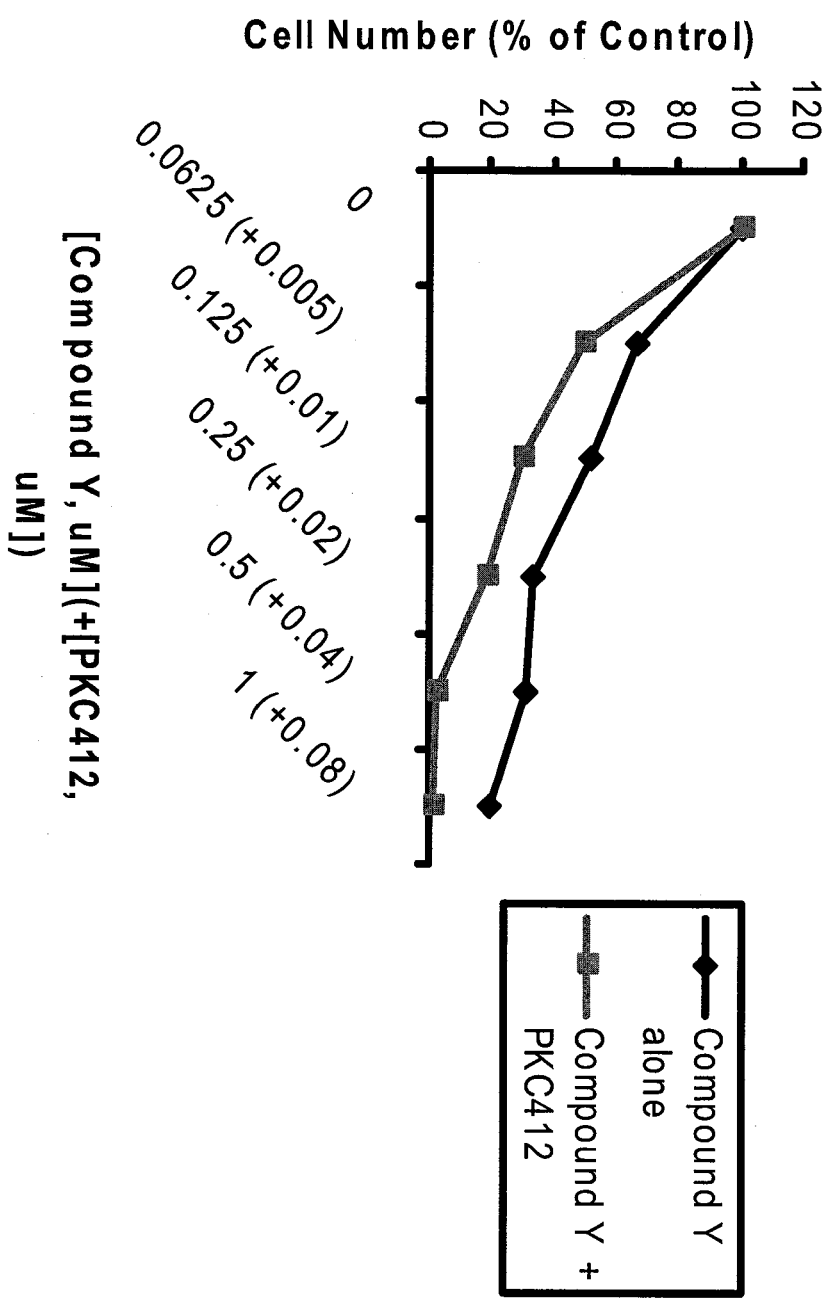

FIG. 12 illustrates proliferation study showing two-day treatment of FLT3-ITD-Ba/F3 cells with (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y), PKC412 or a combination of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and PKC412.

Figure 13:
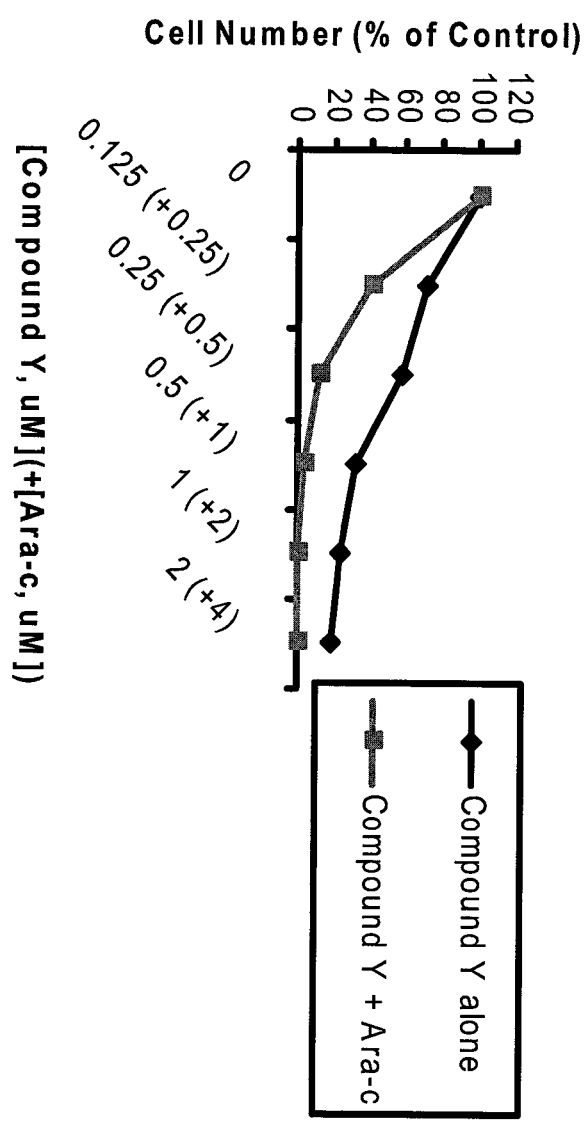

FIG. 13 illustrates proliferation study showing two-day treatment of FLT3-ITD-Ba/F3 cells with (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y), Ara-c, or a combination of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and Ara-c.

Figure 14:
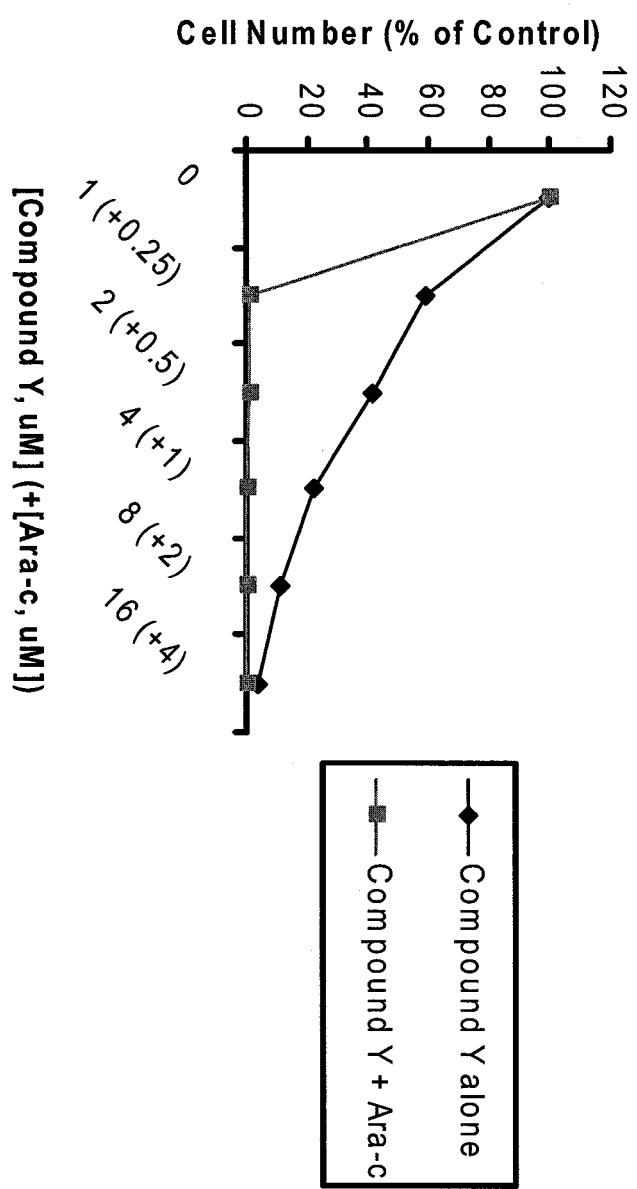

FIG. 14 illustrates proliferation study showing three-day treatment of MOLM13-luc+ cells with (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y), Ara-c or a combination of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and Ara-c.

Figure 15:
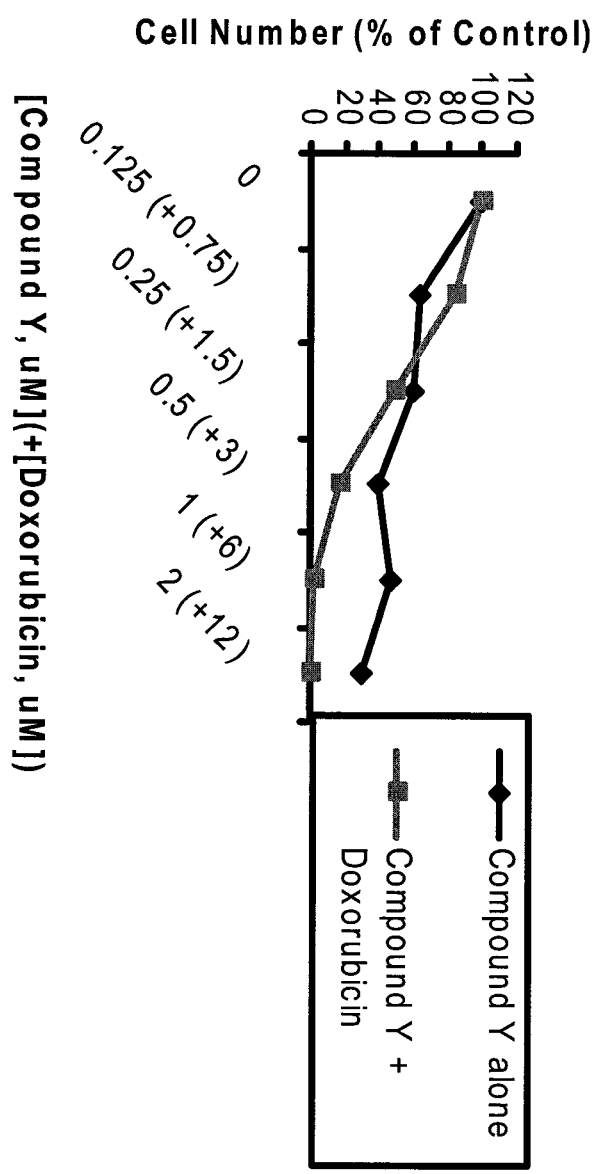

FIG. 15 illustrates proliferation study showing two-day treatment of FLT3-ITD-Ba/F3 cells with (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y), Doxorubicin or a combination of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and Doxorubicin.

Figure 16:
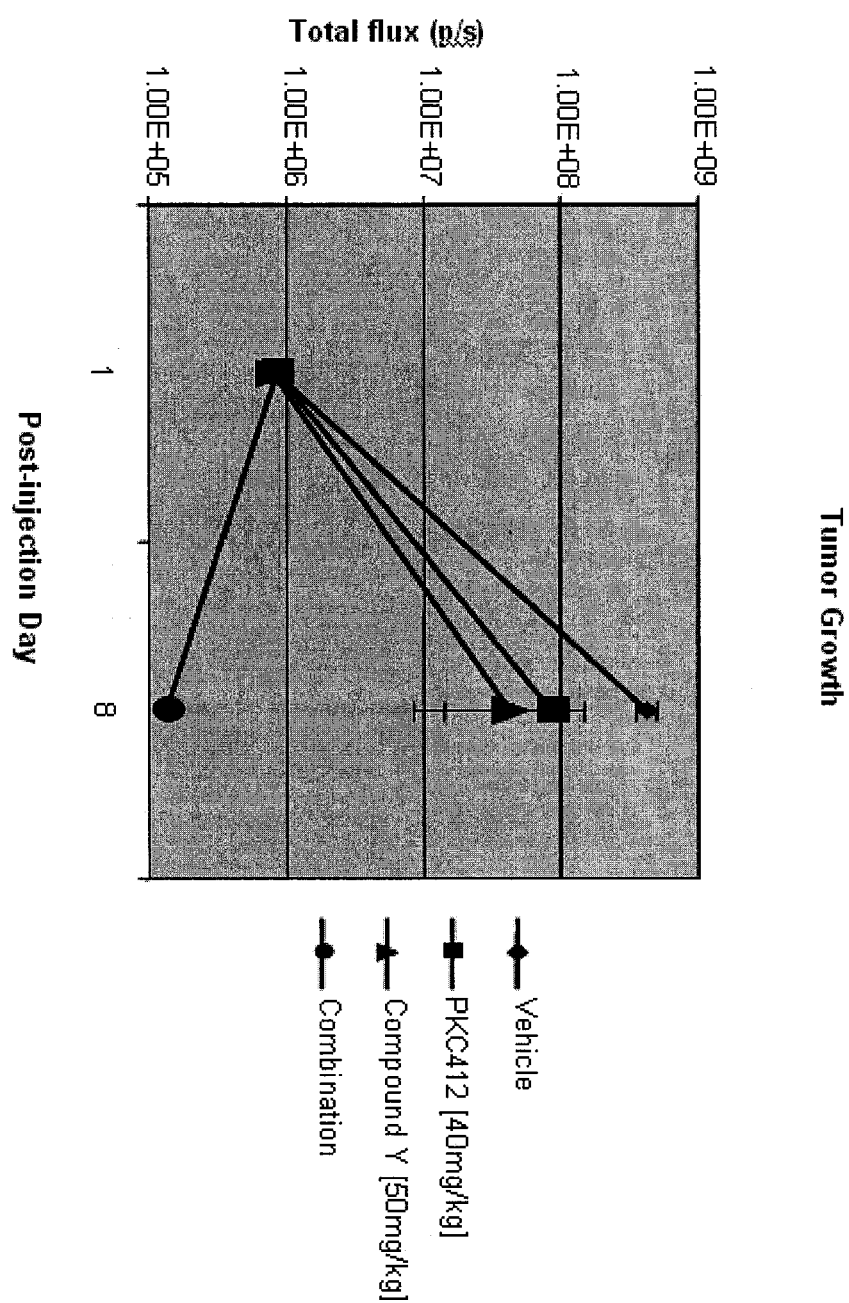

FIG. 16 illustrates the in vivo tumor growth of murine FLT3-ITD-Ba/F3 cells in mice.

DETAILED DESCRIPTION OF THE INVENTION

Protein kinase C, herein after abbreviated as PKC, is one of the key enzymes in cellular signal transduction pathways, and it has a pivotal role in the control of cell proliferation and differentiation. PKC is a family of serine/threonine kinases.

At least 12 isoforms of PKC have been identified, and they are commonly divided into three groups based on their structure and substrate requirements. Promising results have recently been achieved in clinical trials investigating the effects of the protein tyrosine kinase inhibitor PKC412 on AML patients harboring mutations in the FLT3 protein.

Midostaurin is N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methylbenzamide of the formula (II):

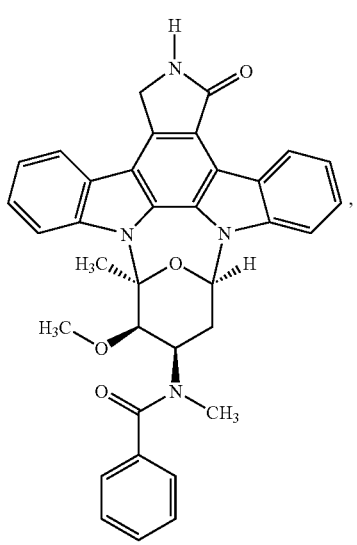

or a salt thereof, hereinafter "Compound of formula II or midostaurin".

Compound of formula (II) or midostaurin [International Nonproprietary Name] is also known as PKC412.

Midostaurin is a derivative of the naturally occurring alkaloid staurosporine, and has been specifically described in the European Patent No. 0 296 110 published on Dec. 21, 1988, as well as in U.S. Pat. No. 5,093,330 published on Mar. 3, 1992, and Japanese Patent No. 2 708 047.

The precise dosage of midostaurin to be employed for treating the diseases and conditions mentioned hereinbefore depends upon several factors including the host, the nature and the severity of the condition being treated, the mode of administration. In general, satisfactory results are achieved when midostaurin is administered parenterally, e.g., intraperitoneally, intravenously, intramuscularly, subcutaneously, intratumorally, or rectally, or enterally, e.g., orally, preferably intravenously or, preferably orally, intravenously at a daily dosage of 0.1-10 mg/kg body weight, preferably 1-5 mg/kg body weight. In human trials a total dose of 225 mg/day was most presumably the Maximum Tolerated Dose (MTD). A preferred intravenous daily dosage is 0.1-10 mg/kg body weight or, for most larger primates, a daily dosage of 200-300 mg. A typical intravenous dosage is 3-5 mg/kg, three to five times a week.

Midostaurin is administered orally in dosages up to about 300 mg/day, e.g., 100-300 mg/day. The midostaurin is administered as a single dose or split into two or three doses daily, preferably two doses. A particularly important dose is 200-225 mg/day, in particular 100 mg twice a day (200 mg/day total). The upper limit of dosage is that imposed by side effects and can be determined by trial for the patient being treated.

PKC412 is an FLT inhibitor because PKC412 interferes with abnormal FLT function by preventing essential proteins from binding to the DNA. A FLT inhibitor blocks the action of the altered FLT gene, rendering it powerless. Other FLT inhibitors include, but are not limited to compounds N-benzoyl-staurosporine, a staurosporine derivative, SU11248 and MLN518.

PCK412 inhibits the growth and viability of mutant FLT3-expressing cells in vitro, and also can extend the lifespan of mice harboring bone marrow transduced with mutant FLT3. See Weisberg et al. (2002). A potential strategy to override the inherent resistance to FLT3 inhibition in patients is to combine structurally unrelated inhibitors and/or inhibitors of different signaling pathways.

Mediators of apoptotic signaling represent an attractive target for therapeutic intervention. Smac mediates apoptosis occurring through the intrinsic apoptotic pathway [see Du et al. (2000)], and binds to and inhibits the IAP family of proteins. See Liu et al. (2000) and Wu et al. (2000).

The inherent resistance of AML to apoptosis suggested that IAPs may be good therapeutic targets in this disease setting and, moreover, that the combination of PKC412 with an IAP inhibitor may be therapeutically beneficial.

Examples of IAP inhibitors for use in the present invention include compound according to formula (I):

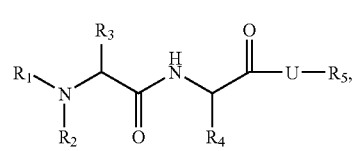

wherein
R$_1$ is H; C$_1$-C$_4$alkyl; C$_1$-C$_4$alkenyl; C$_1$-C$_4$alkynyl or C$_3$-C$_{10}$cycloalkyl which are unsubstituted or substituted;

R$_2$ is H; C$_1$-C$_4$alkyl; C$_1$-C$_4$alkenyl; C$_1$-C$_4$alkynyl or C$_3$-C$_{10}$cycloalkyl which are unsubstituted or substituted;

R$_3$ is H; —CF$_3$; —C$_2$F$_5$; C$_1$-C$_4$alkyl; C$_1$-C$_4$alkenyl; C$_1$-C$_4$alkynyl; —CH$_2$—Z, or R$_2$ and R$_3$, together with the nitrogen, form a het ring;

Z is H; —OH; F; Cl; —CH$_3$; —CF$_3$; —CH$_2$Cl; —CH$_2$F or —CH$_2$OH;

R$_4$ is C$_1$-C$_{16}$straight or branched alkyl; C$_1$-C$_{16}$alkenyl; C$_1$-C$_{16}$alkynyl; or —C$_3$-C$_{10}$cycloalkyl; —(CH$_2$)$_{1-6}$—Z$_1$; —(CH$_2$)$_{0-6}$-arylphenyl; and —(CH$_2$)$_{0-6}$-het, wherein alkyl, cycloalkyl and phenyl are unsubstituted or substituted;

Z$_1$ is —N(R$_8$)—C(O)—C$_1$-C$_{10}$alkyl; —N(R$_8$)—C(O)—(CH$_2$)$_{1-6}$—C$_3$-C$_7$cycloalkyl; —N(R$_8$)—C(O)—(CH$_2$)$_{0-6}$-phenyl; —N(R$_8$)—C(O)—(CH$_2$)$_{1-6}$-het; —C(O)—N(R$_9$)(R$_{10}$); —C(O)—O—C$_1$-C$_{10}$alkyl; —C(O)—O—(CH$_2$)$_{1-6}$—C$_3$-C$_7$cycloalkyl; —C(O)—O—(CH$_2$)$_{0-6}$-phenyl; —C(O)—O—(CH$_2$)$_{1-6}$het; —O—C(O)—C$_1$-C$_{10}$alkyl; —O—C(O)—(CH$_2$)$_{1-6}$—C$_3$-C$_7$cycloalkyl; —O—C(O)—(CH$_2$)$_{0-6}$-phenyl; —O—C(O)—(CH$_2$)$_{1-6}$-het, wherein alkyl, cycloalkyl and phenyl are unsubstituted or substituted;

het is a 5- to 7-membered heterocyclic ring containing 1-4 heteroatoms selected from N, O and S, or an 8- to 12-membered fused ring system including at least one 5- to 7-membered heterocyclic ring containing 1, 2 or 3 heteroatoms selected from N, O and S, which heterocyclic ring or fused ring system is unsubstituted or substituted on a carbon or nitrogen atom;

R$_8$ is H; —CH$_3$; —CF$_3$; —CH$_2$OH or —CH$_2$Cl;

R$_9$ and R$_{10}$ are each independently H; C$_1$-C$_4$alkyl; C$_3$-C$_7$cycloalkyl; —(CH$_2$)$_{1-6}$—C$_3$-C$_7$cycloalkyl; —(CH$_2$)$_{0-6}$-phenyl, wherein alkyl, cycloalkyl and phenyl are unsubstituted or substituted, or R$_9$ and R$_{10}$, together with the nitrogen, form het;

R$_5$ is H; C$_1$-C$_{10}$alkyl; aryl; phenyl; C$_3$-C$_7$cycloalkyl; —(CH$_2$)$_{1-6}$—C$_3$-C$_7$cycloalkyl; —C$_1$-C$_{10}$alkyl-aryl; —(CH$_2$)$_{0-6}$—C$_3$-C$_7$cycloalkyl-(CH$_2$)$_{0-6}$-phenyl; —(CH$_2$)$_{0-4}$CH—((CH$_2$)$_{1-4}$-phenyl)$_2$; —(CH$_2$)$_{0-6}$—CH(phenyl)$_2$; -indanyl; —C(O)—C$_1$-C$_{10}$alkyl; —C(O)—(CH$_2$)$_{1-6}$—C$_3$-C$_7$cycloalkyl; —C(O)—(CH$_2$)$_{0-6}$-phenyl; —(CH$_2$)$_{0-6}$—C(O)-phenyl; —(CH$_2$)$_{0-6}$-het; —C(O)—(CH$_2$)$_{1-6}$-het, or R$_5$ is a residue of an amino acid, wherein the alkyl, cycloalkyl, phenyl and aryl substituents are unsubstituted or substituted;

U is a as shown in structure (III):

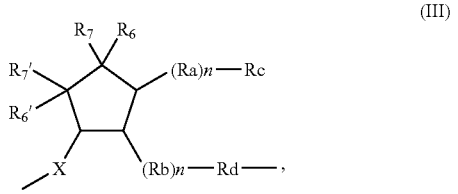

(III)

wherein
n=0-5;
X is —CH or N;
Ra and Rb are independently an O, S or N atom or C$_0$-C$_8$alkyl, wherein one or more of the carbon atoms in the alkyl chain may be replaced by a heteroatom selected from O, S or N, and where the alkyl may be unsubstituted or substituted;

Rd is selected from:
(a) —Re-Q-(Rf)$_p$(Rg)$_q$; or
(b) Ar$_1$-D-Ar$_2$; or
(c) Ar$_1$-D-Ar$_2$;

Rc is H or Rc and Rd may together form a cycloalkyl or het; where if Rd and Rc form a cycloalkyl or het, R$_5$ is attached to the formed ring at a C or N atom;

p and q are independently 0 or 1;

Re is C$_1$-C$_8$alkyl or alkylidene, and Re which may be unsubstituted or substituted;

Q is N, O, S, S(O) or S(O)$_2$;

Ar$_1$ and Ar$_2$ are substituted or unsubstituted aryl or het;

Rf and Rg are each independently none, or H; —C$_1$-C$_{10}$alkyl; C$_1$-C$_{10}$alkylaryl; —OH; —O—C$_1$-C$_{10}$alkyl; —(CH$_2$)$_{0-6}$—C$_3$-C$_7$cycloalkyl; —O—(CH$_2$)$_{0-6}$-aryl; phenyl; aryl; phenyl-phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S—R$_{11}$; —S(O)—R$_{11}$; —S(O)$_2$—R$_{11}$; —S(O)$_2$—NR$_{11}$R$_{12}$; —NR$_{11}$—S(O)$_2$—R$_{12}$; S—C$_1$-C$_{10}$alkyl; aryl-C$_1$-C$_4$alkyl; het-C$_1$-C$_4$alkyl, wherein alkyl, cycloalkyl, het and aryl are unsubstituted or substituted; —SO$_2$-C$_1$-C$_2$alkyl; —SO$_2$-C$_1$-C$_2$alkylphenyl; —O—C$_1$-C$_4$alkyl, or Rg and Rf form a ring selected from het or aryl; and D is —CO—; —C(O)— or C$_1$-C$_7$alkylene or arylene; —CF$_2$—; —O—; -or S(O)$_{rn}$, where rn is 0-2; 1,3dioaxolane; or C$_1$-C$_7$alkyl-OH, where alkyl, alkylene or arylene may be unsubstituted or substituted with one or more halogens, OH, —O—C$_1$-C$_6$alkyl, —S—C$_1$-C$_6$alkyl or —CF$_3$, or D is —N(Rh), wherein Rh is H; C$_1$-C$_7$alkyl (unsubstituted or substituted); aryl; —O(C$_1$-C$_7$cycloalkyl) (unsubstituted or substituted); C(O)—C$_{10}$-C$_{10}$alkyl; C(O)—C$_0$-C$_{10}$alkyl-aryl; C—O—C$_1$-C$_{10}$alkyl; C—O—C$_0$-C$_{10}$alkyl-aryl or SO$_2$—C$_{10}$-C$_{10}$-alkyl; SO$_2$—(C$_0$-C$_{10}$-alkylaryl);

R$_6$, R$_7$, R'$_6$ and R'$_7$ are each independently H; —C$_1$-C$_{10}$alkyl; —C$_1$-C$_{10}$alkoxy; aryl-C$_1$-C$_{10}$alkoxy; —OH; —O—C$_1$-C$_{10}$alkyl; —(CH$_2$)$_{0-6}$—C$_3$-C$_7$cycloalkyl; —O—(CH$_2$)$_{0-6}$-aryl; phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S—R$_{11}$; —S(O)—R$_{11}$; —S(O)$_2$—R$_{11}$; —S(O)$_2$—NR$_{11}$R$_{12}$; —NR$_{11}$—S(O)$_2$—R$_{12}$, wherein alkyl, cycloalkyl and aryl are unsubstituted or substituted; and R$_6$, R$_7$, R'$_6$ and R'$_7$ can be united to form a ring system; and R$_{11}$ and R$_{12}$ are independently H; C$_1$-C$_{10}$alkyl; —(CH$_2$)$_{0-6}$—C$_3$-C$_7$cycloalkyl; —(CH$_2$)$_{0-6}$—(CH)$_{0-1}$(aryl)$_{1-2}$; —C(O)—C$_1$-C$_{10}$alkyl; —C(O)—(CH$_2$)$_{1-6}$—C$_3$-C$_7$cycloalkyl; —C(O)—O—(CH$_2$)$_{0-6}$-aryl; —C(O)—(CH$_2$)$_{0-6}$—O-fluorenyl; —C(O)—NH—(CH$_2$)$_{0-6}$-aryl; —C(O)—(CH$_2$)$_{0-6}$-aryl; —C(O)—(CH$_2$)$_{1-6}$-het; —C(S)—C$_1$-C$_{10}$alkyl; —C(S)—(CH$_2$)$_{1-6}$—C$_3$-C$_7$cycloalkyl; —C(S)—O—(CH$_2$)$_{0-6}$-aryl; —C(S)—(CH$_2$)$_{0-6}$—O-fluorenyl; —C(S)—NH—(CH$_2$)$_{0-6}$-aryl; —C(S)—(CH$_2$)$_{0-6}$-aryl; —C(S)—(CH$_2$)$_{1-6}$-het, wherein alkyl, cycloalkyl and aryl are unsubstituted or substituted, or $R_{11}$ and $R_{12}$ are a substituent that facilitates transport of the molecule across a cell membrane, or $R_{11}$ and $R_{12}$, together with the nitrogen atom, form het, wherein the alkyl substituents of $R_{11}$ and $R_{12}$ may be unsubstituted or substituted by one or more substituents selected from $C_1$-$C_{10}$alkyl, halogen, OH, —O—$C_1$-$C_6$alkyl, —S—$C_1$-$C_6$alkyl or —$CF_3$;

substituted cycloalkyl substituents of $R_{11}$ and $R_{12}$ are substituted by one or more substituents selected from a $C_1$-$C_{10}$ alkene; $C_1$-$C_6$alkyl; halogen; OH; —O—$C_1$-$C_6$alkyl; —S—$C_1$-$C_6$alkyl or —$CF_3$; and substituted phenyl or aryl of $R_{11}$ and $R_{12}$ are substituted by one or more substituents selected from halogen; hydroxy; $C_1$-$C_4$alkyl; $C_1$-$C_4$alkoxy; nitro; —CN; —O—C(O)—$C_1$-$C_4$alkyl and —C(O)—O—$C_1$-$C_4$aryl, or pharmaceutically acceptable salts thereof.

Further examples of IAP inhibitors for use in the present invention include compound of formula (Ia), disclosed in PCT/US2007/074790:

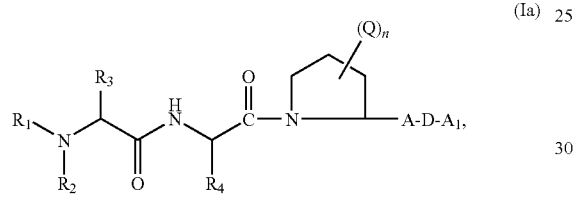

(Ia)

or pharmaceutically acceptable salts thereof,
wherein
$R_1$ is H, $C_1$-$C_4$ alkyl, $C_2$-$C_4$ alkenyl, $C_2$-$C_4$ alkynyl or $C_3$-$C_{10}$ cycloalkyl, which $R_1$ may be unsubstituted or substituted;

$R_2$ is H, $C_1$-$C_4$ alkyl, $C_2$-$C_4$ alkenyl, $C_2$-$C_4$ alkynyl, $C_3$-$C_{10}$ cycloalkyl which $R_2$ may be unsubstituted or substituted;

$R_3$ is H, $CF_3$, $C_2F_5$, $C_1$-$C_4$ alkyl, $C_2$-$C_4$ alkenyl, $C_2$-$C_4$ alkynyl, $CH_2$—Z, or $R_2$ and $R_3$, taken together with the nitrogen atom to which they are attached, form a heterocyclic ring, which alkyl, alkenyl, alkynyl or het ring may be unsubstituted or substituted;

Z is H, OH, F, Cl, $CH_3$, $CH_2Cl$, $CH_2F$ or $CH_2OH$;

$R_4$ is $C_{0-10}$ alkyl, $C_{0-10}$ alkenyl, $C_{0-10}$ alkynyl, $C_3$-$C_{10}$ cycloalkyl, wherein the $C_{0-10}$ alkyl, or cycloalkyl group is unsubstituted or substituted;

A is het, which may be substituted or unsubstituted;

D is $C_1$-$C_7$ alkylene or $C_2$-$C_9$ alkenylene, C(O), O, $NR_7$, S(O)r, C(O)—$C_1$-$C_{10}$ alkyl, O—$C_1$-$C_{10}$ alkyl, S(O)r-$C_1$-$C_{10}$ alkyl, C(O)$C_0$-$C_{10}$ arylalkyl, O$C_0$-$C_{10}$ arylalkyl, or S(O)r$C_0$-$C_{10}$ arylalkyl, which alkyl and aryl groups may be unsubstituted or substituted;

r is 0, 1 or 2;

$A_1$ is a substituted or unsubstituted aryl or unsubstituted or substituted het which substituents on aryl and het are halo, alkyl, lower alkoxy, $NR_5R_6$, CN, $NO_2$ or $SR_5$;

each Q is independently H, $C_1$-$C_{10}$ alkyl, $C_1$-$C_{10}$ alkoxy, aryl$C_1$-$C_{10}$ alkoxy, OH, O—$C_1$-$C_{10}$ alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$ het, het, O—$(CH_2)_{1-6}$ het, —$OR_{11}$, C(O)$R_{11}$, —C(O)N($R_{11}$)($R_{12}$), N($R_{11}$)($R_{12}$), $SR_{11}$, S(O)$R_{11}$, $S(O)_2R_{11}$, $S(O)_2$—N($R_{11}$)($R_{12}$), or $NR_{11}$—$S(O)_2$—($R_{12}$), wherein alkyl, cycloalkyl and aryl are unsubstituted or substituted;

n is 0, 1, 2 or 3, 4, 5, 6 or 7;

het is a 5- to 7-membered monocyclic heterocyclic ring containing 1-4 heteroring atoms selected from N, O and S or an 8- to 12-membered fused ring system that includes one 5- to 7-membered monocyclic heterocyclic ring containing 1, 2 or 3 heteroring atoms selected from N, O and S, which het is unsubstituted or substituted;

$R_{11}$ and $R_{12}$ are independently H, $C_1$-$C_{10}$ alkyl, $(CH_2)_{0-6}$—$C_3$-$C_7$ cycloalkyl, $(CH_2)_{0-6}$—$(CH)_{0-1}$ (aryl)$_{1-2}$, C(O)—$C_1$-$C_{10}$ alkyl, —C(O)—$(CH_2)_{1-6}$—$C_3$-$C_7$ cycloalkyl, —C(O)—O—$(CH_2)_{0-6}$-aryl, —C(O)—$(CH_2)_{0-6}$—O-fluorenyl, C(O)—NH—$(CH_2)_{0-6}$-aryl, C(O)—$(CH_2)_{0-6}$-aryl, C(O)—$(CH_2)_{1-6}$-het, —C(S)—$C_1$-$C_{10}$alkyl, —C(S)—$(CH_2)_{1-6}$—$C_3$-$C_7$ cycloalkyl, —C(S)—O—$(CH_2)_{0-6}$-aryl, —C(S)—$(CH_2)_{0-6}$—O-fluorenyl, C(S)—NH—$(CH_2)_{0-6}$-aryl, —C(S)—$(CH_2)_{0-6}$-aryl or C(S)—$(CH_2)_{1-6}$-het, C(O)$R_{11}$, C(O)$NR_{11}R_{12}$, C(O)$OR_{11}$, S(O)n$R_{11}$, $S(O)_mNR_{11}R_{12}$, m=1 or 2, C(S)$R_{11}$, C(S)$NR_{11}R_{12}$, C(S)$OR_{11}$, wherein alkyl, cycloalkyl and aryl are unsubstituted or substituted; or $R_{11}$ and $R_{12}$ are a substituent that facilitates transport of the molecule across a cell membrane, or $R_{11}$ and $R_{12}$ together with the nitrogen atom form het, wherein
the alkyl substituents of $R_{11}$ and $R_{12}$ may be unsubstituted or substituted by one or more substituents selected from $C_1$-$C_{10}$ alkyl, halogen, OH, O—$C_1$-$C_6$ alkyl, —S—$C_1$-$C_6$ alkyl, $CF_3$ or $NR_{11}R_{12}$;

substituted cycloalkyl substituents of $R_{11}$ and $R_{12}$ are substituted by one or more substituents selected from a $C_2$-$C_{10}$ alkene; $C_1$-$C_6$ alkyl; halogen; OH; O—$C_1$-$C_6$ alkyl; S—$C_1$-$C_6$ alkyl, $CF_3$; or $NR_{11}R_{12}$ and substituted het or substituted aryl of $R_{11}$ and $R_{12}$ are substituted by one or more substituents selected from halogen, hydroxy, $C_1$-$C_4$ alkyl, $C_1$-$C_4$ alkoxy, nitro, CNO—C(O)—$C_1$-$C_4$alkyl and C(O)—O—$C_1$-$C_4$-alkyl;

$R_5$, $R_6$ and $R_7$ are independently hydrogen, lower alkyl, aryl, aryl lower alkyl, cycloalkyl, or cycloalkyl lower alkyl, C(O)$R_5$; S(O)$R_5$, C(O)O$R_5$, C(O)$NR_5R_6$, and the substituents on $R_1$, $R_2$, $R_3$, $R_4$, Q, and A and $A_1$ groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, arylsulfonyl, aryl-lower alkylsulfonyl, lower aryl alkyl lower alkylarylsulfonyl, halogen-lower alkylmercapto, halogen-lower alkylsulfonyl, phosphono (—P(=O)(OH)$_2$), hydroxy-lower alkoxy phosphoryl or di-lower alkoxyphosphoryl, ($R_9$)NC(O)—$NR_{10}R_{13}$, lower alkyl carbamic acid ester or carbamates or —$NR_8R_{14}$, wherein R$_8$ and R$_{14}$ can be the same or different and are independently H or lower alkyl, or R$_8$ and R$_{14}$, together with the N atom, form a 3- to 8-membered heterocyclic ring containing a nitrogen heterocyclic atoms and may optionally contain one or two additional heterocyclic atoms selected from nitrogen, oxygen and sulfur, which heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbarmoyl, N-lower or N,N-dilower alkyl carbamoyl, mercapto, or lower alkylthio; and R$_9$, R$_{10}$ and R$_{13}$ are independently hydrogen, lower alkyl, halogen substituted lower alkyl, aryl, aryl lower alkyl, halogen substituted aryl, halogen substituted aryl lower alkyl.

The preferred compounds are selected from the group consisting of:

(S)-N-((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide;

(S)-N-[(S)-Cyclohexyl-(ethyl-{(S)-1-[5-(4-fluoro-benzoyl)-pyridin-3-yl]-propyl}carbamoyl)-methyl]-2-methylamino-propionamide;

(S)-N-((S)-1-Cyclohexyl-2-{(S)-2-[5-(4-fluoro-phenoxy)-pyridin-3-yl]-pyrrolidin-1-yl}-2-oxo-ethyl)-2-methylamino-propionamide; and N-[1-Cyclohexyl-2-(2-{2-[(4-fluorophenyl)-methyl-amino]-pyridin-4-yl}pyrrolidin-1-yl)-2-oxo-ethyl]-2-methylamino-propinamide;

and pharmaceutically acceptable salts thereof.

Examples of other IAP inhibitors include compounds disclosed in WO 05/097791 published on Oct. 20, 2005, which is hereby incorporated into the present application by reference. A preferred compound within the scope of formula (I) is N-[1-cyclohexyl-2-oxo-2-(6-phenethyl-octahydro-pyrrolo[2,3-c]pyridin-1-yl-ethyl]-2-methylamino-propionamide.

Additional IAP inhibitors include compounds disclosed in WO 04/005284, PCT/US2006/013984 and PCT/US2006/021850 WO. Other IAP inhibitor compounds for use in the present invention include those disclosed in WO 06/069063, WO 05/069888, US2006/0014700, WO 04/007529, US2006/0025347, WO 06/010118, WO 05/069894, WO 06/017295, WO 04/007529 and WO 05/094818.

One of the preferred compounds is compound A, (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide.

Compound A can, for instance be prepared by the following reaction scheme:

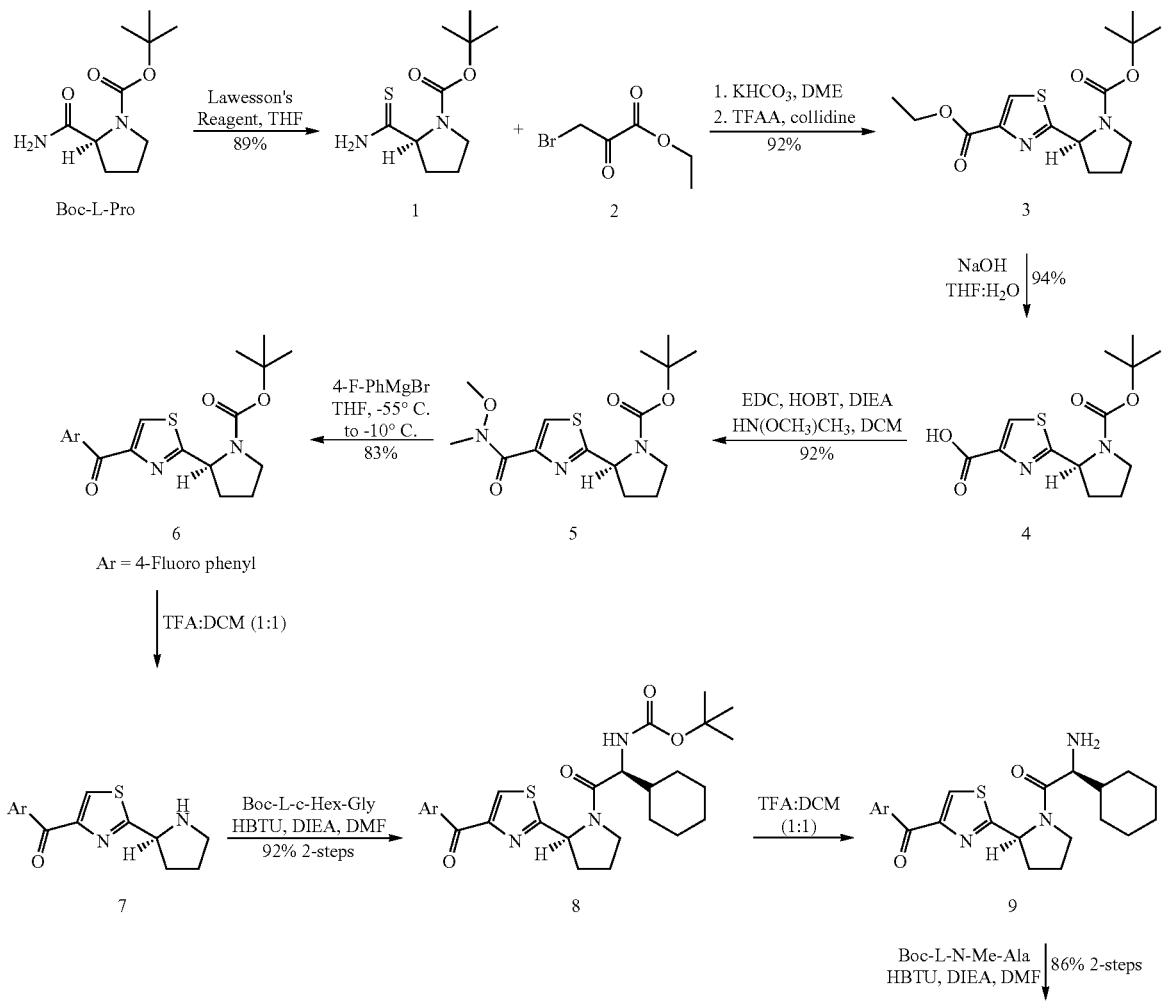

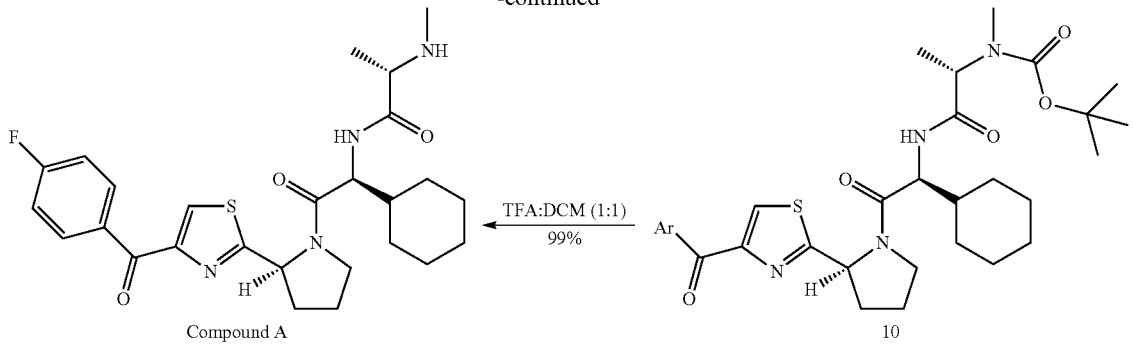

Compound A                              10

As used herein, the term "aryl" is defined as an aromatic radical having 6-14 ring carbon atoms, and no ring heteroatoms. The aryl group may be monocyclic or fused bicyclic or tricyclic. It may be unsubstituted or substituted by one or more, preferably one or two, substituents, wherein the substituents are as described herein. As defined herein, the aryl moiety may be completely aromatic regardless of whether it is monocyclic or bicyclic. However, if it contains more than one ring, as defined herein, the term aryl includes moieties wherein at least one ring is completely aromatic while the other ring(s) may be partially unsaturated or saturated or completely aromatic. Preferred "aryl" is phenyl, naphthyl or indanyl. The most preferred aryl is phenyl.

"Het", as used herein, refers to heteroaryl and heterocyclic compounds containing at least one S, O or N ring heteroatom. More specifically, "het" is a 5- to 7-membered heterocyclic ring containing 1-4 heteroatoms selected from N, O and S, or an 8- to 12-membered fused ring system including at least one 5- to 7-membered heterocyclic ring containing 1, 2 or 3 heteroatoms selected from N, O and S. Examples of het, as used herein, include unsubstituted and substituted pyrrolidyl, tetrahydrofuryl, tetrahydrothiofuryl, piperidyl, piperazyl, purinyl, tetrahydropyranyl, morpholino, 1,3-diazapanyl, 1,4-diazapanyl, 1,4-oxazepanyl, 1,4-oxathiapanyl, furyl, thienyl, pyrryl, pyrrolyl, pyrazolyl, triazolyl, tetrazolyl, indazolyl, oxadiazolyl, imidazolyl, pyrrolidyl, pyrrolidinyl, thiazolyl, oxazolyl, pyridyl, pyrazolyl, pyrazinyl, pyrimidinyl, isoxazolyl, pyrazinyl, quinolyl, isoquinolyl, pyridopyrazinyl, pyrrolopyridyl, furopyridyl, indolyl, benzofuryl, benzothiofuryl, benzoindolyl, benzothienyl, pyrazolyl, piperidyl, piperazinyl, indolinyl, morpholinyl, benzoxazolyl, pyrroloquinolyl, and the like. Heteroaryls are within the scope of the definition of het. Examples of heteroaryls are pyridyl, pyrimidinyl, quinolyl, thiazolyl and benzothiazolyl. The most preferred het are pyridyl, pyrimidinyl and thiazolyl. The het may be unsubstituted or substituted as described herein. It is preferred that it is unsubstituted or if substituted it is substituted on a carbon atom by halogen, especially fluorine or chlorine, hydroxy, $C_1$-$C_4$ alkyl, such as methyl and ethyl, $C_1$-$C_4$ alkoxy, especially methoxy and ethoxy, nitro, —O—C(O)—$C_1$-$C_4$ alkyl or —C(O)—O—$C_1$-$C_4$ alkyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, sulfonate, sulfanyl, SCN or nitro or on a nitrogen atom by $C_1$-$C_4$ alkyl, especially methyl or ethyl, —O—C(O)—$C_1$-$C_4$ alkyl or —C(O)—O—$C_1$-$C_4$ alkyl, such as carbomethoxy or carboethoxy. When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazole, and the like, wherein such het may be unsubstituted or substituted as defined hereinabove.

Halogen is fluorine, chlorine, bromine or iodine, especially fluorine and chlorine.

Unless otherwise specified, "alkyl", either above or in combination, includes straight or branched chain alkyl, such as methyl, ethyl, n-propyl, isopropyl, n-butyl, sec-butyl, tert-butyl, n-pentyl and branched pentyl, n-hexyl and branched hexyl, and the like.

A "cycloalkyl" group means $C_3$-$C_{10}$ cycloalkyl having 3-10 ring carbon atoms and may be, e.g., cyclopropyl, cyclobutyl, cyclopentyl, cyclohexyl, cycloheptyl or cyclooctyl, cyclononyl and the like. The cycloalkyl group may be monocyclic or fused bicyclic. It is preferred that it is monocyclic. Moreover, the preferred cycloalkyl group is cyclopentyl or cyclohexyl. Most preferably, cycloalkyl is cyclohexyl. The cycloalkyl group may be fully saturated or partially unsaturated, although it is preferred that it is fully saturated. As defined herein, it excludes aryl groups. The cycloalkyl groups may be unsubstituted or substituted with any of the substituents defined below, preferably halo, hydroxy or $C_1$-$C_6$ alkyl, such as methyl.

Substituents that facilitate transport of the molecule across a cell membrane are known to those of skill in the medicinal chemistry arts [see, e.g., Gangewar S. et al., *Drug Discov Today*, Vol. 2, pp. 148-155 (1997); and Bundgaard H. and Moss J., *Pharma Res*, Vol. 7, p. 885 (1990)]. Generally, such substituents are lipophilic substituents. Such lipophilic substituents include a $C_6$-$C_{30}$ alkyl which is saturated, monounsaturated, polyunsaturated, including methylene-interrupted polyene, phenyl, phenyl which is substituted by one or two $C_1$-$C_8$ alkyl groups, $C_5$-$C_9$ cycloalkyl, $C_5$-$C_9$ cycloalkyl which is substituted by one or two $C_1$-$C_8$ alkyl groups, —$X_1$-phenyl, —$X_1$-phenyl which is substituted in the phenyl ring by one or two $C_1$-$C_8$ alkyl groups, $X_1$—$C_5$-$C_9$ cycloalkyl or $X_1$—$C_5$-$C_9$ cycloalkyl which is substituted by one or two $C_1$-$C_8$ alkyl groups; where $X_1$ is $C_1$-$C_{24}$ alkyl which is saturated, monounsaturated or polyunsaturated and straight or branched chain.

Unsubstituted is intended to mean that hydrogen is the only substituent.

Except as described herein, any of the above defined aryl, het, alkyl, alkenyl, alkynyl or cycloalkyl, may be unsubstituted or independently substituted by up to four, preferably one, two or three substituents, selected from the group consisting of: halo, such as Cl or Br; hydroxy; lower alkyl, such as $C_1$-$C_3$ alkyl; lower alkyl which may be substituted with any of the substituents defined herein; lower alkenyl; lower alkynyl; lower alkanoyl; lower alkoxy, such as methoxy; aryl, such as phenyl or naphthyl; substituted aryl, such as fluoro phenyl or methoxy phenyl; aryl lower alkyl, such as benzyl, amino, mono or di-lower alkyl, such as dimethylamino; lower alkanoyl amino acetylamino; amino lower alkoxy, such as ethoxyamine; nitro; cyano; cyano lower alkyl; carboxy; lower carbalkoxy, such as methoxy carbonyl; n-propoxy carbonyl or iso-propoxy carbonyl, lower aryloyl, such as benzoyl; carbamoyl; N-mono- or N,N di-lower alkyl carbamoyl; lower alkyl carbamic acid ester; amidino; guanidine; ureido; mercapto; sulfo; lower alkylthio; sulfoamino; sulfonamide; benzosulfonamide; sulfonate; sulfanyl lower alkyl, such as methyl sulfanyl; sulfoamino; aryl sulfonamide; halogen substituted or unsubstituted aryl sulfonate, such as chloro-phenyl sulfonate; lower alkylsulfinyl; arylsulfinyl; aryl-lower alkyl-sulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane alkoxyphosphoryl; urea and substituted urea of the formula $(R_9)NC(O)N(R_{10})$, $(R_{13})$, wherein $R_9$, $R_{10}$ and $R_{13}$ are as defined herein, such as urea or 3-trifluoro-methyl-phenyl urea; alkyl carbamic acid ester or carbamates, such as ethyl-N-phenyl-carbamate; or —$NR_8R_{14}$, wherein $R_8$ and $R_{14}$ can be the same or different and are independently H; lower alkyl, e.g., methyl, ethyl or propyl; or $R_8$ and $R_{14}$, together with the N atom, form a 3- to 8-membered heterocyclic ring containing a nitrogen heteroring atom and optionally one or two additional heteroring atoms selected from the group consisting of nitrogen, oxygen and sulfur (e.g. piperazinyl, pyrazinyl, lower alkyl-piperazinyl, pyridyl, indolyl, thiophenyl, thiazolyl, benzothiophenyl, pyrrolidinyl, piperidino or imidazolinyl) where the heterocyclic ring may be substituted with any of the substituents defined hereinabove.

Preferably the above mentioned alkyl, cycloalkyl, and aryl groups are independently unsubstituted or are substituted by lower alkyl, aryl, aryl lower alkyl, carboxy, lower carbalkoxy and especially halogen, —OH, —SH, —$OCH_3$, —$SCH_3$, —CN, —SCN or nitro.

As defined herein, the term "lower alkyl", when used alone or in combination, refers to alkyl containing 1-6 carbon atoms. The alkyl group may be branched or straight-chained, and is as defined hereinabove.

The term "lower alkenyl" refers to a alkenyl group which contains 2-6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include ethenyl, 1-propenyl, 2-propenyl, 1-butenyl, 2-butenyl, 2-methyl-1-propenyl, 1,3-butadienyl and the like. The preferred alkenyl group is ethenyl.

The term "lower alkynyl", as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. It is preferred that the alkynyl group contains 1 or 2 carbon-carbon triple bonds and more preferably one carbon-carbon triple bond. The alkynyl group may be straight chained or branched. Examples include ethynyl, 1-propynyl, 2-propynyl, 1-butynyl, 2-butynyl and the like. The preferred alkynyl group is ethynyl.

As used herein, the term "aryl alkyl" refers to a aryl group connected to the main chain by a bridging alkylene group. Examples include benzyl, phenethyl, naphthylmethyl, and the like. The preferred aryl alkyl is benzyl. Similarly, cyano alkyl group refers to a cyano group connected to the main chain by a bridging alkylene group.

The term "alkyl aryl" on the other hand, refers to an alkyl group bridged to the main chain through a phenylene group. Examples include methylphenyl, ethylphenyl and the like.

As used herein, the term "lower alkanoyl" refers to a lower alkyl chain in which one of the carbon atoms is replaced by a C=O group. The C=O group may be present at one of the ends of the substituent or in the middle of the moiety. Examples include formyl, acetyl, 2-propanoyl, 1-propanoyl and the like.

The term "alkoxy" refers to an alkyl group as defined herein, connected to the main chain by an oxygen atom. Examples include methoxy, ethoxy and the like.

The term "lower thioalkyl" refers to an alkyl group, as defined herein, connected to the main chain by a sulfur atom. Examples include thiomethyl (or mercapto methyl), thioethyl (mercapto ethyl) and the like.

The term "lower carbalkoxy" or synonym thereto refers to an alkoxycarbonyl group, where the attachment to the main chain is through the aryl group (C(O)). Examples include methoxy carbonyl, ethoxy carbonyl and the like.

It is to be understood that the terminology C(O) refers to a —C=O group, whether it be ketone, aldehyde or acid or acid derivative. Similarly, S(O) refers to a —S=O group.

As used herein, the term S(O)r refers to the number of oxygen atoms bonded to the sulfur atom. When r=2, then $S(O)r=SO_2$, when r is 1, then S(O)r is SO; and when r=O, then S(O)r is S.

The term "$C_0$", as used herein, as part of a definition of alkyl as, e.g., $C_{0-10}$, refers to zero carbon atoms. Thus, "$C_0$-$C_{10}$ aryl alkyl" means that the aryl group is bonded directly to the main chain ($C_0$) or that there is a $C_1$-$C_{10}$ alkylene group bridging the main chain to an aryl group.

The term "$(CH_2)_{0-6}$" as part of definition of a larger group, e.g., $(CH_2)_{0-6}C_3$-$C_7$ cycloalkyl, refers to a group that is not present $(CH_2)_0$, or to a group that contains 1-6 carbon atoms $(CH_2)_{1-6}$.

The term "$(CH_2)_{0-6}$—$(CH)_{0-1}$, $(aryl)_{1-2}$", in the definition of $R_{11}$ and $R_{12}$, is intended to mean one of the following $(CH_2)_{1-6}$-aryl, aryl, —$CH(aryl)_2$ or $(CH_2)_{1-6}(CH) (aryl)_2$.

As used herein, the variable "n" refers to number of substitutents on the pyrrolidinyl (tetrahydropyrrolyl) ring. The term "n" is defined as 0-7 and it determines the number of Q substituents on the pyrrolidinyl (tetrahydro-pyrrolyl) ring. Q can only be present at the 2, 3, 4 or 5 positions of the pyrrolidinyl ring, i.e., at the carbon atoms of the pyrrolidinyl ring. Except for carbon number 2 that can allow for one substitution, each of other carbon atoms are saturated and each of them may have two substituents thereon. When n is 7, then each of the carbon atoms are bonded with Q as defined herein. Each Q may be the same or different. However, when n is 6, then one of the seven possible substituents is H, and the other five are Q, which can be the same or different. Further, when n is 5, then two of the possible substitutents are H, and the other five are independently Q, as defined herein. When n is 4, then three of the seven possible substituents are H, and the remainder are Q independently as defined herein. Where n is 3, then four of the seven possible substituents are H, and the other three are Q as defined herein. When n is 2, then two of the seven possible substituent are Q, and the remainder are H. When n is 1, then only one of the seven possible substituent is Q, and the remainder are H. Finally, when n is 0, all seven of the substituents are H.

It is to be understood that each of the Q substituents may be the same or they may be different.

Where the plural form is used for compounds, salts, pharmaceutical preparations, this is intended to mean also a single compound, single pharmaceutical preparation, salt and the like.

Comprised are likewise the pharmaceutically acceptable salts thereof, the corresponding racemates, diastereoisomers, enantiomers, tautomers, as well as the corresponding crystal modifications of above disclosed compounds where present, e.g., solvates, hydrates and polymorphs, which are disclosed therein.

The precise dosage of an IAP inhibitor compound to be employed depends upon several factors including the host, the nature and the severity of the condition being treated, the mode of administration. The IAP inhibitor compound can be administered by any route including orally, parenterally, e.g., intraperitoneally, intravenously, intramuscularly, subcutaneously, intratumorally, or rectally, or enterally. Preferably, the IAP inhibitor compound is administered orally, preferably at a daily dosage of 1-300 mg/kg body weight or, for most larger primates, a daily dosage of 50-5,000, preferably 500-3,000 mg. A preferred oral daily dosage is 1-75 mg/kg body weight or, for most larger primates, a daily dosage of 10-2,000 mg, administered as a single dose or divided into multiple doses, such as twice daily dosing.

Usually, a small dose is administered initially and the dosage is gradually increased until the optimal dosage for the host under treatment is determined. The upper limit of dosage is that imposed by side effects and can be determined by trial for the host being treated.

Dosage regimens must be titrated to the particular indication, the age, weight and general physical condition of the patient, and the response desired but generally doses will be from about 10 mg/day to about 500 mg/day as needed in single or multiple daily administration.

In one aspect the present invention provides A combination comprising (a) a compound according to formula (I):

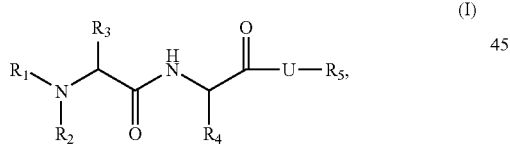

wherein
- $R_1$ is H; $C_1$-$C_4$alkyl; $C_1$-$C_4$alkenyl; $C_1$-$C_4$alkynyl or $C_3$-$C_{10}$cycloalkyl which are unsubstituted or substituted;
- $R_2$ is H; $C_1$-$C_4$alkyl; $C_1$-$C_4$alkenyl; $C_1$-$C_4$alkynyl or $C_3$-$C_{10}$cycloalkyl which are unsubstituted or substituted;
- $R_3$ is H; —$CF_3$; —$C_2F_5$; $C_1$-$C_4$alkyl; $C_1$-$C_4$alkenyl; $C_1$-$C_4$alkynyl; —$CH_2$—Z, or
- $R_2$ and $R_3$, together with the nitrogen, form a het ring;
- Z is H; —OH; F; Cl; —$CH_3$; —$CF_3$; —$CH_2Cl$; —$CH_2F$ or —$CH_2OH$;
- $R_4$ is $C_1$-$C_{16}$straight or branched alkyl; $C_1$-$C_{16}$alkenyl; $C_1$-$C_{16}$alkynyl; or $C_3$-$C_{10}$cycloalkyl; —$(CH_2)_{1-6}$—$Z_1$; —$(CH_2)_{0-6}$-arylphenyl; and —$(CH_2)_{0-6}$-het, wherein alkyl, cycloalkyl and phenyl are unsubstituted or substituted;
- $Z_1$ is —$N(R_8)$—$C(O)$—$C_1$-$C_{10}$alkyl; —$N(R_8)$—$C(O)$—$(CH_2)_{1-6}$—$C_3$-$C_7$cycloalkyl; —$N(R_8)$—$C(O)$—$(CH_2)_{0-6}$-phenyl; —$N(R_8)$—$C(O)$—$(CH_2)_{1-6}$-het; —$C(O)$—$N(R_9)(R_{10})$; —$C(O)$—$O$—$C_1$-$C_{10}$alkyl; —$C(O)$—$O$—$(CH_2)_{1-6}$—$C_3$-$C_7$cycloalkyl; —$C(O)$—$O$—$(CH_2)_{0-6}$-phenyl; —$C(O)$—$O$—$(CH_2)_{1-6}$-het; —$O$—$C(O)$—$C_1$-$C_{10}$alkyl; —$O$—$C(O)$—$(CH_2)_{1-6}$—$C_3$-$C_7$cycloalkyl; —$O$—$C(O)$—$(CH_2)_{0-6}$-phenyl; —$O$—$C(O)$—$(CH_2)_{1-6}$-het, wherein alkyl, cycloalkyl and phenyl are unsubstituted or substituted;
- het is a 5- to 7-membered heterocyclic ring containing 1-4 heteroatoms selected from N, O and S, or an 8- to 12-membered fused ring system including at least one 5- to 7-membered heterocyclic ring containing 1, 2 or 3 heteroatoms selected from N, O and S, which heterocyclic ring or fused ring system is unsubstituted or substituted on a carbon or nitrogen atom;
- $R_8$ is H; —$CH_3$; —$CF_3$; —$CH_2OH$ or —$CH_2Cl$;
- $R_9$ and $R_{10}$ are each independently H; $C_1$-$C_4$alkyl; $C_3$-$C_7$cycloalkyl; —$(CH_2)_{1-6}$—$C_3$-$C_7$cycloalkyl; —$(CH_2)_{0-6}$-phenyl, wherein alkyl, cycloalkyl and phenyl are unsubstituted or substituted, or
- $R_9$ and $R_{10}$, together with the nitrogen, form het;
- $R_5$ is H; $C_1$-$C_{10}$alkyl; aryl; phenyl; $C_3$-$C_7$cycloalkyl; —$(CH_2)_{1-6}$—$C_3$-$C_7$cycloalkyl; —$C_1$-$C_{10}$alkyl-aryl; —$(CH_2)_{0-6}$—$C_3$-$C_7$cycloalkyl-$(CH_2)_{0-6}$-phenyl; —$(CH_2)_{0-4}CH$—$((CH_2)_{1-4}$-phenyl)$_2$; —$(CH_2)_{0-6}$—$CH$(phenyl)$_2$; -indanyl; —$C(O)$—$C_1$-$C_{10}$alkyl; —$C(O)$—$(CH_2)_{1-6}$—$C_3$-$C_7$cycloalkyl; —$C(O)$—$(CH_2)_{0-6}$-phenyl; —$(CH_2)_{0-6}$—$C(O)$-phenyl; —$(CH_2)_{0-6}$-het; —$C(O)$—$(CH_2)_{1-6}$-het, or
- $R_5$ is a residue of an amino acid, wherein the alkyl, cycloalkyl, phenyl and aryl substituents are unsubstituted or substituted;
- U is a as shown in structure (III):

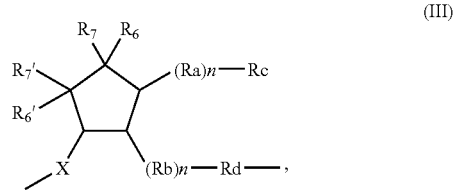

wherein
- n=0-5;
- X is —CH or N;
- Ra and Rb are independently an O, S or N atom or $C_0$-$C_8$alkyl, wherein one or more of the carbon atoms in the alkyl chain may be replaced by a heteroatom selected from O, S or N, and where the alkyl may be unsubstituted or substituted;
- Rd is selected from:
    (a) —Re-Q-(Rf)$_p$(Rg)$_q$; or
    (b) Ar$_1$-D-Ar$_2$; or
    (c) Ar$_1$-D-Ar$_2$;
- Rc is H or Rc and Rd may together form a cycloalkyl or het; where if Rd and Rc form a cycloalkyl or het, $R_5$ is attached to the formed ring at a C or N atom;
- p and q are independently 0 or 1;
- Re is $C_1$-$C_8$alkyl or alkylidene, and Re which may be unsubstituted or substituted;
- Q is N, O, S, S(O) or S(O)$_2$;
- Ar$_1$ and Ar$_2$ are substituted or unsubstituted aryl or het;

Rf and Rg are each independently none, or H; —$C_1$-$C_{10}$alkyl; $C_1$-$C_{10}$alkylaryl; —OH; —O—$C_1$-$C_{10}$alkyl; —$(CH_2)_{0-6}$—$C_3$-$C_7$cycloalkyl; —O—$(CH_2)_{0-6}$-aryl; phenyl; aryl; phenyl-phenyl; —$(CH_2)_{1-6}$-het; —O—$(CH_2)_{1-6}$-het; —$OR_{11}$; —C(O)—$R_{11}$; —C(O)—N($R_{11}$)($R_{12}$); —N($R_{11}$)($R_{12}$); —S—$R_{11}$; —S(O)—$R_{11}$; —S(O)$_2$—$R_{11}$; —S(O)$_2$—$NR_{11}R_{12}$; —$NR_{11}$—S(O)$_2$—$R_{12}$; S—$C_1$-$C_{10}$alkyl; aryl-$C_1$-$C_4$alkyl; het-$C_1$-$C_4$alkyl, wherein alkyl, cycloalkyl, het and aryl are unsubstituted or substituted; —SO$_2$-$C_1$-$C_2$alkyl; —SO$_2$-$C_1$-$C_2$alkylphenyl; —O—$C_1$-$C_4$alkyl, or Rg and Rf form a ring selected from het or aryl; and D is —CO—; —C(O)— or $C_1$-$C_7$alkylene or arylene; —CF$_2$—; —O—; -or S(O)$_{nr}$, where rn is 0-2; 1,3dioxaxolane; or $C_1$-$C_7$alkyl-OH, where alkyl, alkylene or arylene may be unsubstituted or substituted with one or more halogens, OH, —O—$C_1$-$C_6$alkyl, —S—$C_1$-$C_6$alkyl or —CF$_3$, or D is —N(Rh), wherein Rh is H; $C_1$-$C_7$alkyl (unsubstituted or substituted); aryl; —O($C_1$-$C_7$cycloalkyl) (unsubstituted or substituted); C(O)—$C_{10}$-$C_{10}$alkyl; C(O)—$C_0$-$C_{10}$alkylaryl; C—O—$C_1$-$C_{10}$alkyl; C—O—$C_0$-$C_{10}$alkyl-aryl or SO$_2$—$C_{10}$-$C_{10}$-alkyl; SO$_2$—($C_0$-$C_{10}$-alkylaryl);

$R_6$, $R_7$, $R'_6$ and $R'_7$ are each independently H; —$C_1$-$C_{10}$alkyl; —$C_1$-$C_{10}$alkoxy; aryl-$C_1$-$C_{10}$alkoxy; —OH; —O—$C_1$-$C_{10}$alkyl; —$(CH_2)_{0-6}$—$C_3$-$C_7$cycloalkyl; —O—$(CH_2)_{0-6}$-aryl; phenyl; —$(CH_2)_{1-6}$-het; —O—$(CH_2)_{1-6}$-het; —$OR_{11}$; —C(O)—$R_{11}$; —C(O)—N($R_{11}$)($R_{12}$); —N($R_{11}$)($R_{12}$); —S—$R_{11}$; —S(O)—$R_{11}$; —S(O)$_2$—$R_{11}$; —S(O)$_2$—$NR_{11}R_{12}$; —$NR_{11}$—S(O)$_2$—$R_{12}$, wherein alkyl, cycloalkyl and aryl are unsubstituted or substituted; and $R_6$, $R_7$, $R'_6$ and $R'_7$ can be united to form a ring system; and $R_{11}$ and $R_{12}$ are independently H; $C_1$-$C_{10}$alky; —$(CH_2)_{0-6}$—$C_3$-$C_7$cycloalkyl; —$(CH_2)_{0-6}$—$(CH)_{0-1}$(aryl)$_{1-2}$; —C(O)—$C_1$-$C_{10}$alkyl; —C(O)—$(CH_2)_{1-6}$—$C_3$-$C_7$cycloalkyl; —C(O)—O—$(CH_2)_{0-6}$-aryl; —C(O)—$(CH_2)_{0-6}$—O-fluorenyl; —C(O)—NH—$(CH_2)_{0-6}$-aryl; —C(O)—$(CH_2)_{0-6}$-aryl; —C(O)—$(CH_2)_{1-6}$-het; —C(S)—$C_1$-$C_{10}$alkyl; —C(S)—$(CH_2)_{1-6}$—$C_3$-$C_7$cycloalkyl; —C(S)—O—$(CH_2)_{0-6}$-aryl; —C(S)—$(CH_2)_{0-6}$—O-fluorenyl; —C(S)—NH—$(CH_2)_{0-6}$-aryl; —C(S)—$(CH_2)_{0-6}$-aryl; —C(S)—$(CH_2)_{1-6}$-het, wherein alkyl, cycloalkyl and aryl are unsubstituted or substituted, or $R_{11}$ and $R_{12}$ are a substituent that facilitates transport of the molecule across a cell membrane, or $R_{11}$ and $R_{12}$, together with the nitrogen atom, form het, wherein the alkyl substituents of $R_{11}$ and $R_{12}$ may be unsubstituted or substituted by one or more substituents selected from $C_1$-$C_{10}$alkyl, halogen, OH, —O—$C_1$-$C_6$alkyl, —S—$C_1$-$C_6$alkyl or —CF$_3$;

substituted cycloalkyl substituents of $R_{11}$ and $R_{12}$ are substituted by one or more substituents selected from a $C_1$-$C_{10}$ alkene; $C_1$-$C_6$alkyl; halogen; OH; —O—$C_1$-$C_6$alkyl; —S—$C_1$-$C_6$alkyl or —CF$_3$; and substituted phenyl or aryl of $R_{11}$ and $R_{12}$ are substituted by one or more substituents selected from halogen; hydroxy; $C_1$-$C_4$alkyl; $C_1$-$C_4$alkoxy; nitro; —CN; —O—C(O)—$C_1$-$C_4$alkyl and —C(O)—O—$C_1$-$C_4$aryl, or pharmaceutically acceptable salts thereof, or a compound of formula Ia

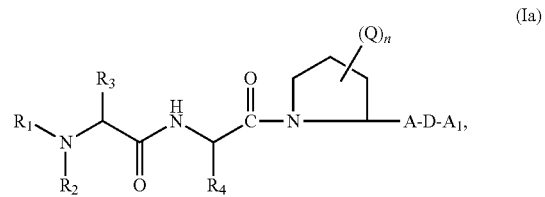

or pharmaceutically acceptable salts thereof,
wherein $R_1$ is H, $C_1$-$C_4$ alkyl, $C_2$-$C_4$ alkenyl, $C_2$-$C_4$ alkynyl or $C_3$-$C_{10}$ cycloalkyl, which $R_1$ may be unsubstituted or substituted;

$R_2$ is H, $C_1$-$C_4$ alkyl, $C_2$-$C_4$ alkenyl, $C_2$-$C_4$ alkynyl, $C_3$-$C_{10}$ cycloalkyl which $R_2$ may be unsubstituted or substituted;

$R_3$ is H, CF$_3$, $C_2$F$_5$, $C_1$-$C_4$ alkyl, $C_2$-$C_4$ alkenyl, $C_2$-$C_4$ alkynyl, CH$_2$—Z, or $R_2$ and $R_3$, taken together with the nitrogen atom to which they are attached, form a heterocyclic ring, which alkyl, alkenyl, alkynyl or het ring may be unsubstituted or substituted;

Z is H, OH, F, Cl, CH$_3$, CH$_2$Cl, CH$_2$F or CH$_2$OH;

$R_4$ is $C_{0-10}$ alkyl, $C_{0-10}$ alkenyl, $C_{0-10}$ alkynyl, $C_3$-$C_{10}$ cycloalkyl, wherein the $C_{0-10}$ alkyl, or cycloalkyl group is unsubstituted or substituted;

A is het, which may be substituted or unsubstituted;

D is $C_1$-$C_7$ alkylene or $C_2$-$C_9$ alkenylene, C(O), O, NR$_7$, S(O)r, C(O)—$C_1$-$C_{10}$ alkyl, O—$C_1$-$C_{10}$ alkyl, S(O)r-$C_1$-$C_{10}$ alkyl, C(O)$C_0$-$C_{10}$ arylalkyl, OC$_0$-$C_{10}$ arylalkyl, or S(O)r$C_0$-$C_{10}$ arylalkyl, which alkyl and aryl groups may be unsubstituted or substituted;

r is 0, 1 or 2;

$A_1$ is a substituted or unsubstituted aryl or unsubstituted or substituted het which substituents on aryl and het are halo, alkyl, lower alkoxy, NR$_5$R$_6$, CN, NO$_2$ or SR$_5$;

each Q is independently H, $C_1$-$C_{10}$ alkyl, $C_1$-$C_{10}$ alkoxy, aryl$C_1$-$C_{10}$ alkoxy, OH, O—$C_1$-$C_{10}$ alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$ het, het, O—$(CH_2)_{1-6}$ het, —OR$_{11}$, C(O)R$_{11}$, —C(O)N(R$_{11}$)(R$_{12}$), N(R$_{11}$)(R$_{12}$), SR$_{11}$, S(O)R$_{11}$, S(O)$_2$R$_{11}$, S(O)$_2$—N(R$_{11}$)(R$_{12}$), or NR$_{11}$—S(O)$_2$—(R$_{12}$), wherein alkyl, cycloalkyl and aryl are unsubstituted or substituted;

n is 0, 1, 2 or 3, 4, 5, 6 or 7;

het is a 5- to 7-membered monocyclic heterocyclic ring containing 1-4 heteroring atoms selected from N, O and S or an 8- to 12-membered fused ring system that includes one 5- to 7-membered monocyclic heterocyclic ring containing 1, 2 or 3 heteroring atoms selected from N, O and S, which het is unsubstituted or substituted;

$R_{11}$ and $R_{12}$ are independently H, $C_1$-$C_{10}$ alkyl, $(CH_2)_{0-6}$—$C_3$-$C_7$ cycloalkyl, $(CH_2)_{0-6}$—$(CH)_{0-1}$(aryl)$_{1-2}$, C(O)—$C_1$-$C_{10}$ alkyl, —C(O)—$(CH_2)_{1-6}$—$C_3$-$C_7$ cycloalkyl, —C(O)—O—$(CH_2)_{0-6}$-aryl, —C(O)—$(CH_2)_{0-6}$—O-fluorenyl, C(O)—NH—$(CH_2)_{0-6}$-aryl, C(O)—$(CH_2)_{0-6}$-aryl, C(O)—$(CH_2)_{1-6}$-het, —C(S)—$C_1$-$C_{10}$alkyl, —C(S)—

(CH$_2$)$_{1-6}$—C$_3$-C$_7$ cycloalkyl, —C(S)—O—(CH$_2$)$_{0-6}$-aryl, —C(S)—(CH$_2$)$_{0-6}$—O-fluorenyl, C(S)—NH—(CH$_2$)$_{0-6}$-aryl, —C(S)—(CH$_2$)$_{0-6}$-aryl or C(S)—(CH$_2$)$_{1-6}$-het, C(O)R$_{11}$, C(O)NR$_{11}$R$_{12}$, C(O)OR$_{11}$, S(O)nR$_{11}$, S(O)$_m$NR$_{11}$R$_{12}$, m=1 or 2, C(S)R$_{11}$, C(S)NR$_{11}$R$_{12}$, C(S)OR$_{11}$, wherein alkyl, cycloalkyl and aryl are unsubstituted or substituted; or R$_{11}$ and R$_{12}$ are a substituent that facilitates transport of the molecule across a cell membrane, or R$_{11}$ and R$_{12}$ together with the nitrogen atom form het, wherein the alkyl substituents of R$_{11}$ and R$_{12}$ may be unsubstituted or substituted by one or more substituents selected from C$_1$-C$_{10}$ alkyl, halogen, OH, O—C$_1$-C$_6$ alkyl, —S—C$_1$-C$_6$ alkyl, CF$_3$ or NR$_{11}$R$_{12}$;

substituted cycloalkyl substituents of R$_{11}$ and R$_{12}$ are substituted by one or more substituents selected from a C$_2$-C$_{10}$ alkene; C$_1$-C$_6$ alkyl; halogen; OH; O—C$_1$-C$_6$ alkyl; S—C$_1$-C$_6$ alkyl, CF$_3$; or NR$_{11}$R$_{12}$ and substituted het or substituted aryl of R$_{11}$ and R$_{12}$ are substituted by one or more substituents selected from halogen, hydroxy, C$_1$-C$_4$ alkyl, C$_1$-C$_4$ alkoxy, nitro, CNO—C(O)—C$_1$-C$_4$alkyl and C(O)—O—C$_1$-C$_4$-alkyl;

R$_5$, R$_6$ and R$_7$ are independently hydrogen, lower alkyl, aryl, aryl lower alkyl, cycloalkyl, or cycloalkyl lower alkyl, C(O)R$_5$; S(O)R$_5$, C(O)OR$_5$, C(O)NR$_5$R$_6$, and the substituents on R$_1$, R$_2$, R$_3$, R$_4$, Q, and A and A$_1$ groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, arylsulfonyl, aryl-lower alkylsulfonyl, lower aryl alkyl lower alkylarylsulfonyl, halogen-lower alkylmercapto, halogen-lower alkylsulfonyl, phosphono (—P(=O)(OH)$_2$), hydroxy-lower alkoxy phosphoryl or di-lower alkoxyphosphoryl, (R$_9$)NC(O)—NR$_{10}$R$_{13}$, lower alkyl carbamic acid ester or carbamates or —NR$_8$R$_{14}$, wherein R$_8$ and R$_{14}$ can be the same or different and are independently H or lower alkyl, or R$_8$ and R$_{14}$, together with the N atom, form a 3- to 8-membered heterocyclic ring containing a nitrogen heteroring atoms and may optionally contain one or two additional heteroring atoms selected from nitrogen, oxygen and sulfur, which heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbarmoyl, N-lower or N,N-dilower alkyl carbamoyl, mercapto, or lower alkylthio; and R$_9$, R$_{10}$ and R$_{13}$ are independently hydrogen, lower alkyl, halogen substituted lower alkyl, aryl, aryl lower alkyl, halogen substituted aryl, halogen substituted aryl lower alkyl.

in combination with one or more of the following:

(b) a compound of the formula (II):

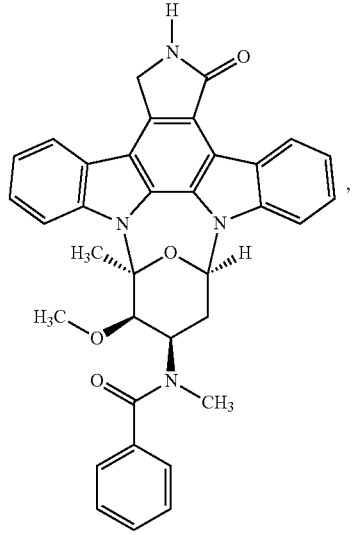

or a salt thereof;

(c) doxorubicin; and (d) cytarabine.

In another aspect the invention provides a combination comprising compound (I) and compound (II), doxorubicin or cytarabine. Compound (I) may be N-[1-cyclohexyl-2-oxo-2-(6-phenethyl-octahydro-pyrrolo[2,3-c]pyridin-1-yl-ethyl]-2-methylamino-propionamide.

In a further aspect the invention provides a combination comprising compound (Ia) and compound (II), doxorubicin or cytarabine. Compound (Ia) may be (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide.

In a further aspect the present invention provides a pharmaceutical composition comprising compound (I) or (Ia) and compound (II), doxorubicin or cytarabine. Compound (I) may be N-[1-cyclohexyl-2-oxo-2-(6-phenethyl-octahydro-pyrrolo[2,3-c]pyridin-1-yl-ethyl]-2-methylamino-propionamide and compound (Ia) may be (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide.

In another aspect the present invention provides a pharmaceutical composition comprising compound (I) or (Ia) in combination with a pharmaceutical composition comprising compound (II), doxorubicin or cytarabine. Compound (I) may be N-[1-cyclohexyl-2-oxo-2-(6-phenethyl-octahydro-pyrrolo[2,3-c]pyridin-1-yl-ethyl]-2-methylamino-propionamide and compound (Ia) may be (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide.

The proapoptotic IAP inhibitors, N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide, enhance the killing of PKC412-sensitive and resistant cell lines expressing mutant FLT3 when combined with either PKC412 or standard cytotoxic agents (doxorubicin and Ara-c) in vitro and in vivo.

In addition, the combination of N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide and PKC412 overrides stromal-mediated viability signaling conferring resistance to PKC412.

N-[1-Cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide also enhances the antiproliferative effects of standard chemotherapeutic agents, such as a topoisomerase inhibitor, including doxorubicin, and an antimetabolite, including cytarabine, also known as Ara-c.

N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide enhance the antiproliferative effects of doxorubicin or Ara-c in vitro in PKC412-sensitive and resistant cells.

The term "a topoisomerase inhibitor", includes a topoisomerase I inhibitor and a topoisomerase II inhibitor. Examples of a topoisomerase I inhibitor include, but are not limited to, topotecan, gimatecan, irinotecan, camptothecian and its analogues, 9-nitrocamptothecin and the macromolecular camptothecin conjugate PNU-166148; 10-hydroxycamptothecin acetate salt; etoposide; idarubicin hydrochloride; irinotecan hydrochloride; teniposide; topotecan hydrochloride; doxorubicin; epirubicin hydrochloride; mitoxantrone hydrochloride; and daunorubicin hydrochloride. Irinotecan can be administered, e.g., in the form as it is marketed, e.g., under the trademark CAMPTOSAR. Topotecan can be administered, e.g., in the form as it is marketed, e.g., under the trademark HYCAMTIN. The term "topoisomerase II inhibitor", as used herein, includes, but is not limited to, the anthracyclines, such as doxorubicin, including liposomal formulation, e.g., CAELYX, daunorubicin, including liposomal formulation, e.g., DAUNOSOME, epirubicin, idarubicin and nemorubicin; the anthraquinones mitoxantrone and losoxantrone; and the podophillotoxines etoposide and teniposide. Etoposide is marketed as ETOPOPHOS; teniposide as VM 26-BRISTOL; doxorubicin as ADRIBLASTIN or ADRIAMYCIN; epirubicin as FARMORUBICIN; idarubicin as ZAVEDOS; and mitoxantrone as NOVANTRON.

The term "an anti-metabolite", as used herein, relates to a compound which inhibits or disrupts the synthesis of DNA resulting in cell death. Examples of an antimetabolite include, but are not limited to, 6-mercaptopurine; cytarabine; fludarabine; flexuridine; fluorouracil; capecitabine; raltitrexed; methotrexate; cladribine; gemcitabine; gemcitabine hydrochloride; thioguanine; hydroxyurea; DNA de-methylating agents, such as 5-azacytidine and decitabine; edatrexate; and folic acid antagonists, such as, but not limited to, pemetrexed. Capecitabine can be administered, e.g., in the form as it is marketed, e.g., under the trademark XELODA; and gemcitabine as GEMZAR. Cytarabine is a shortened form of cytosine arabinoside, a commonly used chemotherapy agent used mainly in the treatment of leukemia and non-Hodgkin lymphoma. It is also known as Ara-C, Cytosar®-U, Tarabine® PFS or other local brand names.

The terms "treatment" or "therapy" refer to the prophylactic or preferably therapeutic including, but not limited to, palliative, curing, symptom-alleviating, symptom-reducing, regulating and/or inhibiting, treatment of said diseases, especially of the diseases mentioned below.

The term "AML", as used herein, relates to an uncontrolled, quickly progressing growth of myeloid cells, e.g. granulocytes, as well as erythroid and megakaryotic cells and progenitors. In patients with AML, the immature myeloid, erythroid or megakaryotic cells severely outnumber erythrocytes (red blood cells) leading to fatigue and bleeding, and also to increased susceptibility to infection. In children, as well as in adults, AML has a poor prognosis despite the use of aggressive chemotherapeutic protocols. Overall survival rates are 40-60%. Autologous bone marrow transplant preceded by myeloablative chemotherapy does not change the survival but an allogeneic bone marrow transplant preceded by aggressive chemotherapy might increase the survival rates up to 70%. Unfortunately, the availability of a matched sibling donor is limited. Therefore, new therapeutic strategies in AML treatment are necessary.

A warm-blooded animal (or patient) is preferably a mammal, especially a human or a juvenile human.

N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide synergistically enhance the antiproliferative effects of PKC412 against mutant FLT3-expressing cells. In combination experiments involving N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide and PKC412, additive to synergistic effects between the two compounds are observed in combination against a variety of PKC412-sensitive and resistant cell lines in vitro. A positive cooperative effect is observed in an in vivo imaging model of acute leukemia when mice are treated with a combination of N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide and PKC412; tumor burden is observed to be lowest in NCr nude mice IV-injected with FLT3-ITD-Ba/F3-luc+ expressing cells and treated with the combination of agents, as compared with vehicle or each agent alone.

Small numbers of leukemic CD34+ cells can persist in the marrow microenvironment of patients with CML following years of therapy with imatinib. Similarly, clinical studies of patients with advanced AML receiving FLT3 kinase inhibitors reveal that a common pattern of response was dramatic fall in the circulating population of blasts, with minimal or delayed decrease in marrow blasts, suggesting a protective environment. These observations suggest that a greater understanding of the interaction of stromal cells with leukemic cells is essential. Stromal-mediated chemoresistance of mutant FLT3-expressing cells to PKC412 can be overcome by treatment of cells with an IAP inhibitor, showing a possible role of IAPs in growth factor-mediated signaling leading to PKC412 resistance.

FLT3 regulation of a panel of apoptosis signaling proteins, including Bcl-2, Bcl-XL, and the strong N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide IAP substrates, XIAP and CIAP1 are studied. Only modest changes in XIAP, Bcl-2 and Bcl-XL in FLT3-transformed cells as compared to parental cells. These small changes in protein expression may have some significance in the susceptibility of FLT3-transformed cells to the cytotoxic effects of an inhibitor of protein tyrosine kinases, such as PKC412, or an IAP inhibitor, such as N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide, as well as the enhanced cytotoxic effects of the two agents combined.

In conclusion, N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide are effective against mutant FLT3 at doses that are physiologically achievable and well-tolerated in vivo. N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide also enhances the inhibitory effects of PKC412, as well as standard chemotherapeutic agents, such as doxorubicin and Ara-c, by acting in an additive-synergistic fashion against mutant FLT3-expressing cells in vitro. The ability of N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide and PKC412 (or doxorubicin or Ara-c) to combine additively or synergistically in PKC412-resistant mutant FLT3-expressing cells suggests that IAP inhibitors like N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide could potentially be used in conjunction with other agents to achieve a higher degree of patient responsiveness by suppressing the emergence of drug-resistant FLT3 mutations.

Therefore in another aspect the present invention provides a method of treating a warm-blooded animal having acute myeloid leukemia (AML) or acute myeloid leukemia (AML) which is resistant to conventional chemotherapy comprising administering to said animal a therapeutically effective amount of a combination of compound (I) or (Ia) and compound (II), doxorubicin or cytarabine. Compound (I) may be N-[1-cyclohexyl-2-oxo-2-(6-phenethyl-octahydro-pyrrolo[2,3-c]pyridin-1-yl-ethyl]-2-methylamino-propionamide and compound (Ia) may be (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide.

In a further aspect the invention provides the use of a combination or a pharmaceutical composition comprising compound (I) or (Ia) and compound (II), doxorubicin or cytarabine for the treatment of acute myeloid leukemia (AML) or acute myeloid leukemia which is resistant to conventional chemotherapy. Compound (I) may be N-[1-cyclohexyl-2-oxo-2-(6-phenethyl-octahydro-pyrrolo[2,3-c]pyridin-1-yl-ethyl]-2-methylamino-propionamide and compound (Ia) may be (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide.

In a further aspect the invention provides the use of a combination or a pharmaceutical composition comprising compound (I) or (Ia) and compound (II), doxorubicin or cytarabine for the preparation of a medicament for the treatment of acute myeloid leukemia (AML) or acute myeloid leukemia which is resistant to conventional chemotherapy. Compound (I) may be N-[1-cyclohexyl-2-oxo-2-(6-phenethyl-octahydro-pyrrolo[2,3-c]pyridin-1-yl-ethyl]-2-methylamino-propionamide and compound (Ia) may be (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide In another aspect a commercial package comprising the combination or the pharmaceutical composition comprising compound (I) or (Ia) and compound (II), doxorubicin or cytarabine together with instructions for simultaneous, separate or sequential use thereof in the treatment of AML. Compound (I) may be N-[1-cyclohexyl-2-oxo-2-(6-phenethyl-octahydro-pyrrolo[2,3-c]pyridin-1-yl-ethyl]-2-methylamino-propionamide and compound (Ia) may be (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide.

For the following examples, PKC412 and N-[1-cyclohexyl-2-oxo-2-(6-phenethyl-octahydro-pyrrolo[2,3-c]pyridin-1-yl-ethyl]-2-methylamino-propionamide or (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide are synthesized by Novartis Pharma AG, Basel, Switzerland, and dissolved in DMSO to make 10 mM stock solutions. Serial dilutions are then made, also in DMSO, to obtain final dilutions for cellular assays.

EXAMPLE 1

Preparation of Cell Lines and Cell Culture

The IL-3-dependent murine hematopoietic cell line Ba/F3 was transduced with either FLT3-ITD or FLT3-D835Y-containing MSCV retroviruses harboring a neomycin selectable marker, and selected for resistance to neomycin. See Kelly et al. (2002). FLT3-ITD transduced cells were selected for growth in G418 (1 mg/mL). PKC412-resistant Ba/F3 cell lines, which express FLT3-ITD harboring a mutation in the ATP-binding pocket (F691L, A627T, G697R, N676D), were developed as described previously. See Cools et al. (2004). The human AML-derived, FLT3-ITD-expressing cell line, MV4;11 [see Quentmeier et al. (2003)], was provided to us by Dr. Scott Armstrong, Dana Farber Cancer Institute, Boston, Mass. The human AML-derived, FLT3-ITD-expressing cell line, MOLM-13, was modified to express luciferase and provided to us as MOLM13-luc+ by Dr. Andrew Kung, Dana Farber Cancer Institute, Boston, Mass. All cell lines were cultured with 5% $CO_2$ at 37° C., at a concentration of $2\times10^5$ to $5\times10^5$ in RPMI (Mediatech, Inc., Herndon, Va.) with 10% fetal calf serum and supplemented with 1% glutamine. Parental Ba/F3 cells expressing wild-type FLT3 were similarly cultured with 15% WEHI-conditioned medium as a source of IL-3. All transfected cell lines were cultured in media supplemented with 1 mg/mL G418.

EXAMPLE 2

Antibodies and Immunoblotting

The XIAP (clone 28?) antibody (BD Sciences, Franklin Lakes, N.J.), the CIAP1 antibody (Cell Signaling Technology, Danvers, Mass.), the Bcl-2 (c-2) antibody (Santa Cruz Biotechnology, Santa Cruz, Calif.), and the Bcl-XL (H-5) antibody (Santa Cruz Biotechnology, Santa Cruz, Calif.), were each used at a dilution of 1:200. The monoclonal anti-β-actin antibody (clone AC-15) was purchased from Sigma-Aldrich (St. Louis, Mo.), and was used at a dilution of 1:2000. The α-tubulin (clone DM1A) antibody was purchased from Sigma Aldrich (St. Louis, Mo.) and was used at a 1:2000 dilution. The protein lysis preparation and immunoblotting were carried out as previously described. See Weisberg et al. (2002).

EXAMPLE 3

Cell Viability and Apoptosis Analysis

The trypan blue exclusion assay has been previously described [see Weisberg et al. (2002)], and was used to determine proliferation of cells cultured in the presence and absence of PKC412 and N-[1-cyclohexyl-2-oxo-2-(6-phenethyl-octahydro-pyrrolo[2,3-c]pyridin-1-yl-ethyl]-2-methylamino-propionamide (LBW242). Cell viability is reported as percentage of control (untreated) cells. Error bars represent the standard error of the mean for each data point. Apoptosis of drug-treated cells was measured using the Annexin-V-Fluos Staining Kit (Boehringer Mannheim, Indianapolis, Ind.), as previously described. See Weisberg et al. (2002).

EXAMPLE 4

Human Stroma Experiments

HS-5 human stromal cells (10,000/well) were seeded 24 hours in advance of seeding of MOLM13-luc+ cells (40,000/well), followed by treatment with a range of concentrations of N-[1-cyclohexyl-2-oxo-2-(6-phenethyl-octahydro-pyrrolo[2,3-c]pyridin-1-yl-ethyl]-2-methylamino-propionamide (LBW242) and PKC412, alone and combined. Cells were then analyzed for luciferase expression using a Xenogen imager.

EXAMPLE 5

Drug Combination Studies

For drug combination studies, PKC412 and N-[1-cyclohexyl-2-oxo-2-(6-phenethyl-octahydro-pyrrolo[2,3-c]pyridin-1-yl-ethyl]-2-methylamino-propionamide (LBW242) are added simultaneously at fixed ratios to FLT3-ITD-Ba/F3 cells and PKC412-resistant mutant FLT3-expressing cells. Cell viability is determined using the Trypan blue exclusion assay, and expressed as the function of growth affected (FA) drug-treated versus control cells; data is analyzed by Calcusyn software (Biosoft, Ferguson, Mo. and Cambridge, UK), using the Chou-Talalay method. See Chou and Talalay et al. (1984). The combination index=$[D]_1[D_x]_1+[D]_2/[D_x]_2$, where $[D]_1$ and $[D]_2$ are the concentrations required by each drug in combination to achieve the same effect as concentrations $[D_x]_1$ and $[D_x]_2$ of each drug alone. Values less than one indicate synergy, whereas values greater than one indicate antagonism.

EXAMPLE 6

Mouse Studies and In Vivo Imaging

FLT3-ITD-Ba/F3 cells were transduced with a retrovirus encoding firefly luciferase (MSCV-Luc), and selected with neomycin to generate the FLT3-ITD-Ba/F3-luciferase (luc+) cell line. Cells free of *Mycoplasma* and viral contamination were resuspended in Hank's Balanced Salt Solution (HBSS; Mediatech, Inc., VA) prior to IV administration to mice. 6% w/w PKC412 in Gelucire® 44/14 (Gattefosse, France) was diluted with 1xPBS and warmed in a 42° C. water bath until liquid. The solution was then stored at 4° C. until used for gavage treatment of mice. N-[1-cyclohexyl-2-oxo-2-(6-phenethyl-octahydro-pyrrolo[2,3-c]pyridin-1-yl-ethyl]-2-methylamino-propionamide (LBW242) was prepared by first wetting 10 mg powder stock with 30 µL water, and then dissolving in two equivalents (0.73 µL/mg of compound) of 6.0 N HCl. The resulting (clear) solution was brought up to 1 mL in pH 4.6 acetate buffer, and the resulting stock was stored frozen at −20° C. until used for gavage treatment of mice.

Male NCr-nude mice (5-6 weeks of age; Taconic, N.Y.) were administered a total of 800,000 FLT3-ITD-Ba/F3-luc+ cells by tail vein injection. Mice were imaged and total body luminescence quantified as previously described. See Armstrong et al. (2003). Baseline imaging one day after tumor cell inoculation was used to establish treatment cohorts with matched tumor burden. Cohorts of mice were treated with oral administration of vehicle, 40 mg/kg/day PKC412 (formulated as above), 50 mg/kg N-[1-cyclohexyl-2-oxo-2-(6-phenethyl-octahydro-pyrrolo[2,3-c]pyridin-1-yl-ethyl]-2-methylamino-propionamide (LBW242) (formulated as above), or a combination of PKC412 and N-[1-cyclohexyl-2-oxo-2-(6-phenethyl-octahydro-pyrrolo[2,3-c]pyridin-1-yl-ethyl]-2-methylamino-propionamide (LBW242). Repeat imaging was performed at various intervals. At the planned end of the study (approximately one week following initial IV injection of FLT3-ITD-Ba/F3-luc+ cells), mice were sacrificed, body and spleen weights were recorded, and tissues were preserved in 10% formalin for histopathological analysis.

EXAMPLE 7

Combination Effects of N-[1-cyclohexyl-2-oxo-2-(6-phenethyl-octahydro-pyrrolo[2,3-c]pyridin-1-yl-ethyl]-2-methylamino-propionamide (LBW242) and PKC412 Against PKC412-Sensitive and Resistant Cells N-[1-cyclohexyl-2-oxo-2-(6-phenethyl-octahydro-pyrrolo[2,3-c]pyridin-1-yl-ethyl]-2-methylamino-propionamide (LBW242) is tested in combination with PKC412 against FLT3-ITD-Ba/F3 cells. Positive enhancement effects are observed between the two agents, see FIG. 1 and the following Table I, which shows the combination indices calculated for dose-response curves shown in FIGS. 1 and 2. Analysis of the combined effects of N-[1-cyclohexyl-2-oxo-2-(6-phenethyl-octahydro-pyrrolo[2,3-c]pyridin-1-yl-ethyl]-2-methylamino-propionamide (LBW242) and PKC412 using Calcusyn software shows synergistic effects across a range of doses (ED50-ED90), as depicted in Table I. N-[1-cyclohexyl-2-oxo-2-(6-phenethyl-octahydro-pyrrolo[2,3-c]pyridin-1-yl-ethyl]-2-methylamino-propionamide (LBW242) and PKC412 are also tested in combination against the human acute leukemia, FLT3-ITD-expressing cell line, MV4;11 cell line, and both agents are found to enhance inhibition of cellular proliferation as compared to each drug alone only at higher doses, as depicted in Table I. Calcusyn analysis of the combined effects of N-[1-cyclohexyl-2-oxo-2-(6-phenethyl-octahydro-pyrrolo[2,3-c]pyridin-1-yl-ethyl]-2-methylamino-propionamide (LBW242) and PKC412 suggests moderate synergy to synergy at higher doses (ED75-ED90), with antagonism observed at lower doses (ED50) as depicted in Table I. The combined effects of N-[1-cyclohexyl-2-oxo-2-(6-phenethyl-octahydro-pyrrolo[2,3-c]pyridin-1-yl-ethyl]-2-methylamino-propionamide (LBW242) and PKC412 are also investigated against the PKC412-resistant, mutant FLT3 expressing cell lines, A627T-FLT3-Ba/F3, F691I-FLT3-Ba/F3, G697R-FLT3-Ba/F3, and N676D-FLT3-Ba/F3. Synergistic effects are observed for N-[1-cyclohexyl-2-oxo-2-(6-phenethyl-octahydro-pyrrolo[2,3-c]pyridin-1-yl-ethyl]-2-methylamino-propionamide (LBW242) and PKC412 against the A627T-FLT3-Ba/F3 and F691I-FLT3-Ba/F3 lines (ED50-ED90), and synergy is observed for N-[1-cyclohexyl-2-oxo-2-(6-phenethyl-octahydro-pyrrolo[2,3-c]pyridin-1-yl-ethyl]-2-methylamino-propionamide (LBW242) and PKC412 against the G697R-FLT3-Ba/F3 line (ED50-ED90), please refer to FIG. 2 and Table I. For the N676D-FLT3-Ba/F3 cell line, combination results show an additive effect (ED50-ED90) between N-[1-cyclohexyl-2-oxo-2-(6-phenethyl-octahydro-pyrrolo[2,3-c]pyridin-1-yl-ethyl]-2-methylamino-propionamide (LBW242) and PKC412, as depicted in Table I.

TABLE I

| Cell Lines | Combination Indices: | | |
|---|---|---|---|
| | ED50 | ED75 | ED90 |
| FLT3-ITD-Ba/F3 | 0.74780 | 0.58808 | 0.47158 |
| MV4;11 | 1.98810 | 0.75339 | 0.40562 |
| A627T-Ba/F3 | 0.55582 | 0.40946 | 0.36244 |
| F691I-Ba/F3 | 0.63409 | 0.43267 | 0.30145 |
| G697R-Ba/F3 | 0.39783 | 0.43210 | 0.47464 |
| N676D-Ba/F3 | 1.06409 | 1.04265 | 1.02238 |

EXAMPLE 8

Proliferation Studies Show Combination Effects of N-[1-cyclohexyl-2-oxo-2-(6-phenethyl-octahydro-pyrrolo[2,3-c]pyridin-1-yl-ethyl]-2-methylamino-propionamide (LBW242) and Doxorubicin or Ara-c, Respectively, Against PKC412-Sensitive and Resistant Mutant FLT3-Expressing Cells The combined effects between PKC412 and standard chemotherapy agents, such as doxorubicin and Ara-c, against FLT3-ITD-Ba/F3 cells show synergy for the combination of PKC412 and doxorubicin across a range of doses (ED50-ED90), see FIG. 3 and Table II, which shows the combination indices calculated for dose-response curves shown in FIGS. 3 and 4. Calcusyn analysis of the combined effects of N-[1-cyclohexyl-2-oxo-2-(6-phenethyl-octahydro-pyrrolo[2,3-c]pyridin-1-yl-ethyl]-2-methylamino-propionamide (LBW242) and doxorubicin against FLT3-ITD-Ba/F3 cells shows synergistic effects across a range of doses (ED50-ED90), see FIG. 4 and Table II. Results of Calcusyn analysis of the combined effects of N-[1-cyclohexyl-2-oxo-2-(6-phenethyl-octahydro-pyrrolo[2,3-c]pyridin-1-yl-ethyl]-2-methylamino-propionamide (LBW242) and doxorubicin against F691I-FLT3-Ba/F3 cells show additive to synergistic effects only across the higher range of doses (ED75-ED90), see Table II. For A627T-FLT3-Ba/F3 cells, N-[1-cyclohexyl-2-oxo-2-(6-phenethyl-octahydro-pyrrolo[2,3-c]pyridin-1-yl-ethyl]-2-methylamino-propionamide (LBW242) and doxorubicin were found to act in synergy (ED50-ED90), see Table II. Synergy is observed between N-[1-cyclohexyl-2-oxo-2-(6-phenethyl-octahydro-pyrrolo[2,3-c]pyridin-1-yl-ethyl]-2-methylamino-propionamide (LBW242) and Ara-c for FLT3-ITD-Ba/F3 cells (ED50-ED90), see FIG. 5 and Table II and for F691I-FLT3-Ba/F3 cells and A627T-FLT3-Ba/F3 cells (ED50-ED90), see Table II.

TABLE II

| Cell Lines | Combination Indices: | | |
|---|---|---|---|
| | ED50 | ED75 | ED90 |
| FLT3-ITD-Ba/F3 (LBW242 + Ara-c) | 0.60784 | 0.45149 | 0.33535 |
| A627T-Ba/F3 (LBW242 + Ara-c) | 0.70378 | 0.52217 | 0.38742 |
| F691I-Ba/F3 (LBW242 + Ara-c) | 0.60377 | 0.47024 | 0.41785 |
| FLT3-ITD-Ba/F3 (LBW242 + doxorubici) | 0.89723 | 0.81295 | 0.73688 |
| A627T-Ba/F3 (LBW242 + doxorubici) | 0.38613 | 0.35638 | 0.35964 |
| F691I-Ba/F3 (LBW242 + doxorubici) | 1.35772 | 0.92381 | 0.67332 |
| FLT3-ITD-Ba/F3 (PKC412 + doxorubicin) | 0.66838 | 0.69476 | 0.72401 |
| FLT3-ITD-Ba/F3 (PKC412 + Ara-c) | 1.35975 | 1.17660 | 1.02362 |

EXAMPLE 9

Figure 6:
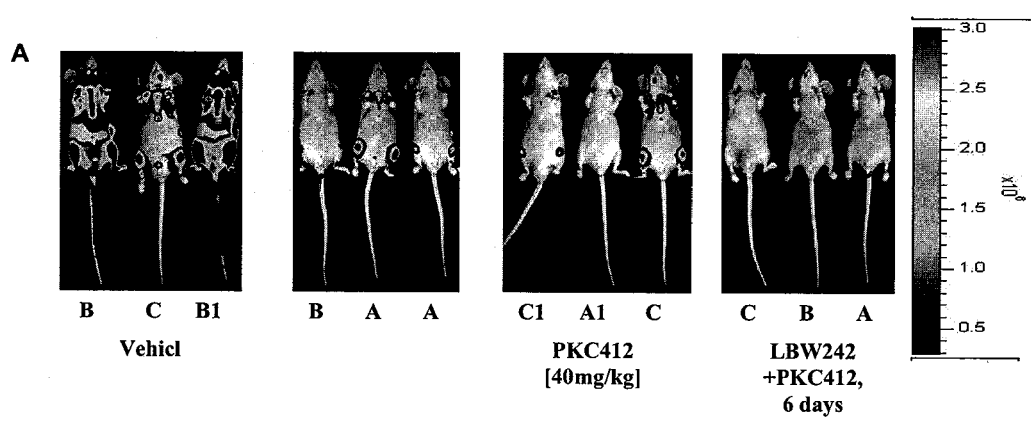
FIG. 6 illustrates in vivo investigation of combined effects of PKC412 and N-[1-cyclohexyl-2-oxo-2-(6-phenethyl-octahydro-pyrrolo[2,3-c]pyridin-1-yl-ethyl]-2-methylamino-propionamide (LBW242); bioluminescence imaging reflects tumor burden following 7 days post-IV injection.

In Vivo Investigation of Effects of N-[1-cyclohexyl-2-oxo-2-(6-phenethyl-octahydro-pyrrolo[2,3-c]pyridin-1-yl-ethyl]-2-methylamino-propionamide (LBW242) and PKC412, Alone and Combined To directly assess the in vivo anti-tumor efficacy of N-[1-cyclohexyl-2-oxo-2-(6-phenethyl-octahydro-pyrrolo[2,3-c]pyridin-1-yl-ethyl]-2-methylamino-propionamide (LBW242) alone, PKC412 alone, and the combination of N-[1-cyclohexyl-2-oxo-2-(6-phenethyl-octahydro-pyrrolo[2,3-c]pyridin-1-yl-ethyl]-2-methylamino-propionamide (LBW242) and PKC412, a mouse model of acute leukemia is studied in which tumor burden is quantified by non-invasive imaging of luminescent tumor cells FIG. 6.

Murine FLT3-ITD-Ba/F3 cells are engineered to stably express firefly luciferase, and NCr nude mice are then inoculated with these cells. Non-invasive imaging is used to serially assess tumor burden, and mice with established leukemia are divided into cohorts with similar tumor burden.

PKC412, N-[1-cyclohexyl-2-oxo-2-(6-phenethyl-octahydro-pyrrolo[2,3-c]pyridin-1-yl-ethyl]-2-methylamino-propionamide (LBW242) or PKC412 combined with N-[1-cyclohexyl-2-oxo-2-(6-phenethyl-octahydro-pyrrolo[2,3-c]pyridin-1-yl-ethyl]-2-methylamino-propionamide (LBW242) are then administered via oral gavage, as is the vehicle. Administration of both agents together is performed by gavaging with one agent approximately 20-30 minutes prior to gavaging with the other agent.

Mice are given vehicle alone, N-[1-cyclohexyl-2-oxo-2-(6-phenethyl-octahydro-pyrrolo[2,3-c]pyridin-1-yl-ethyl]-2-methylamino-propionamide (LBW242) (50 mg/kg), PKC412 (40 mg/kg) or a combination of both N-[1-cyclohexyl-2-oxo-2-(6-phenethyl-octahydro-pyrrolo[2,3-c]pyridin-1-yl-ethyl]-2-methylamino-propionamide (LBW242) and PKC412, see FIG. 6.

Figure 7:
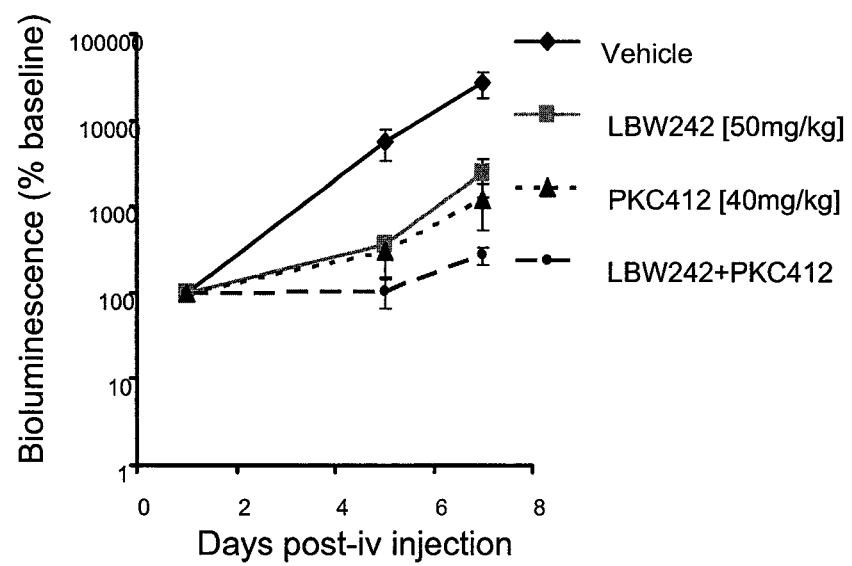
FIG. 7 illustrates graph depiction of FIG. 6 presented as percent baseline.
Figure 8:
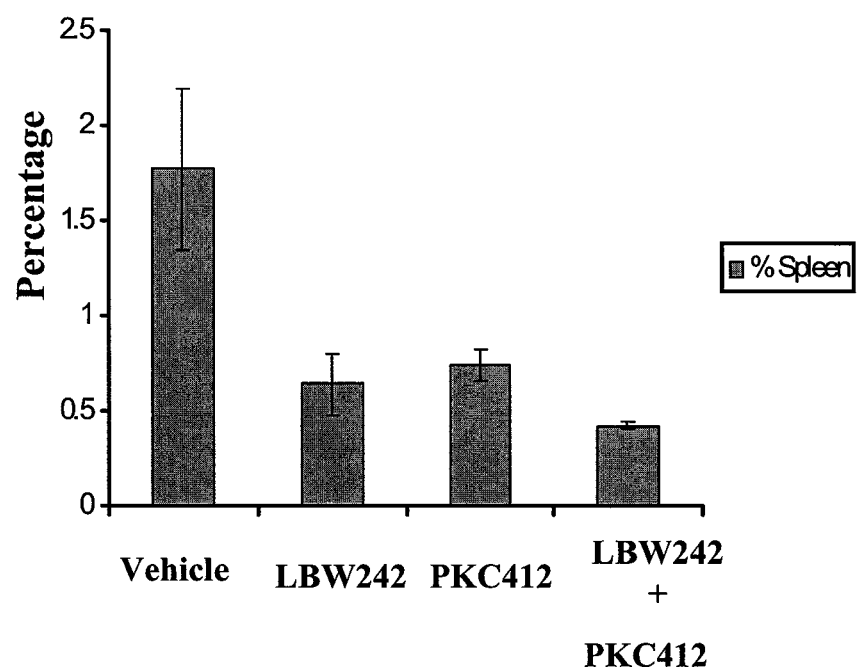
FIG. 8 illustrates the percent spleen weights of mice treated for 10 days with N-[1-cyclohexyl-2-oxo-2-(6-phenethyl-octahydro-pyrrolo[2,3-c]pyridin-1-yl-ethyl]-2-methylamino-propionamide (LBW242), PKC412 or a combination of N-[1-cyclohexyl-2-oxo-2-(6-phenethyl-octahydro-pyrrolo[2,3-c]pyridin-1-yl-ethyl]-2-methylamino-propionamide (LBW242) and PKC412.

The lowest tumor burden as assessed by bioluminescence is observed to be in the drug combination group on days 5 and 7 post-IV injection of FLT3-ITD-Ba/F3-luc+ cells (and corresponding to 4 and 6 days of drug treatment, respectively), see FIGS. 6 and 7. The Student t-test is used for statistical evaluation of bioluminescence results as observed on day 7 post-IV injection: $p<0.056247$ (vehicle versus N-[1-cyclohexyl-2-oxo-2-(6-phenethyl-octahydro-pyrrolo[2,3-c]pyridin-1-yl-ethyl]-2-methylamino-propionamide (LBW242)

alone); p<0.04825 (vehicle versus PKC412 alone); p<0.04329 (vehicle versus N-[1-cyclohexyl-2-oxo-2-(6-phenethyl-octahydro-pyrrolo[2,3-c]pyridin-1-yl-ethyl]-2-methylamino-propionamide (LBW242) and PKC412, combined). Statistical evaluation (via Student t-test) for day 5 post-IV injection yielded: p<0.077299 (vehicle versus N-[1-cyclohexyl-2-oxo-2-(6-phenethyl-octahydro-pyrrolo[2,3-c]pyridin-1-yl-ethyl]-2-methylamino-propionamide (LBW242) alone); p<0.075852 (vehicle versus PKC412 alone); p<0.06826 (vehicle versus N-[1-cyclohexyl-2-oxo-2-(6-phenethyl-octahydro-pyrrolo[2,3-c]pyridin-1-yl-ethyl]-2-methylamino-propionamide (LBW242) and PKC412, combined). Lowest percent spleen weights are observed in mice treated with the combination of N-[1-cyclohexyl-2-oxo-2-(6-phenethyl-octahydro-pyrrolo[2,3-c]pyridin-1-yl-ethyl]-2-methylamino-propionamide (LBW242) and PKC412 following sacrifice 8 days after the last imaging day, see FIG. 8.

EXAMPLE 10

Effects of N-[1-cyclohexyl-2-oxo-2-(6-phenethyl-octahydro-pyrrolo[2,3-c]pyridin-1-yl-ethyl]-2-methylamino-propionamide (LBW242) on Stromal-Mediated Resistance of Mutant FLT3-Expressing Cells to PKC412

The responsiveness of Ba/F3-FLT3-ITD cells cultured in the presence and absence of WEHI (used as a source of IL-3) is studied to the cytotoxic effects of PKC412, and it is found that the presence of IL-3 completely protects cells from PKC412-inhibition of cellular proliferation (supplementary data).

In contrast to PKC412, the IAP inhibitor, N-[1-cyclohexyl-2-oxo-2-(6-phenethyl-octahydro-pyrrolo[2,3-c]pyridin-1-yl-ethyl]-2-methylamino-propionamide (LBW242), inhibits proliferation of Ba/F3-FLT3-ITD cells in both the absence, as well as the presence of IL-3. Interestingly, simultaneous administration of N-[1-cyclohexyl-2-oxo-2-(6-phenethyl-octahydro-pyrrolo[2,3-c]pyridin-1-yl-ethyl]-2-methylamino-propionamide (LBW242) and PKC412 synergistically inhibits the growth of Ba/F3-FLT3-ITD cells cultured in the presence of IL-3; this inhibition is similar in extent to that achieved with co-administration of both agents in the absence of IL-3 suggesting that an IAP inhibitor is able to enhance the effects of a FLT3 inhibitor and override chemoresistance due to provision of viability signals.

Human stromal cell lines, HS-5 are used in combination with the mutant FLT3 AML line, MOLM-13. In order to measure only the leukemic component, luciferase is introduced into the leukemic cells so that the viable cell number using light emission is specifically quantitate. In the study shown in FIG. 9, MOLM-13-luc+ cells (40,000/well) are exposed to PKC412 in the presence or absence of a near confluent monolayer of HS-5 stromal cells. The stromal cell line enhances growth and is partially protective against the inhibitory effects of PKC412, see FIG. 9. As seen with Ba/F3-FLT3-ITD, positive cooperation between PKC412 and N-[1-cyclohexyl-2-oxo-2-(6-phenethyl-octahydro-pyrrolo[2,3-c]pyridin-1-yl-ethyl]-2-methylamino-propionamide (LBW242) in the killing of the human FLT3-ITD-expressing cell line, MOLM13-luc+, is observed in the absence of growth factor. N-[1-cyclohexyl-2-oxo-2-(6-phenethyl-octahydro-pyrrolo[2,3-c]pyridin-1-yl-ethyl]-2-methylamino-propionamide (LBW242) similarly enhances the cytotoxic effects of PKC412 against MOLM13-luc+ cells in both the absence of HS-5 human stromal cells, as well as their presence (see FIG. 9B). These results support the notion that stromal-mediated viability signals may contribute to chemoresistance to FLT3 inhibitors (such as PKC412) observed in marrow, and that such resistance may be overcome by inclusion of IAP inhibitor treatment.

EXAMPLE 11

Mutant FLT3 Regulation of IAPs

Figure 10:
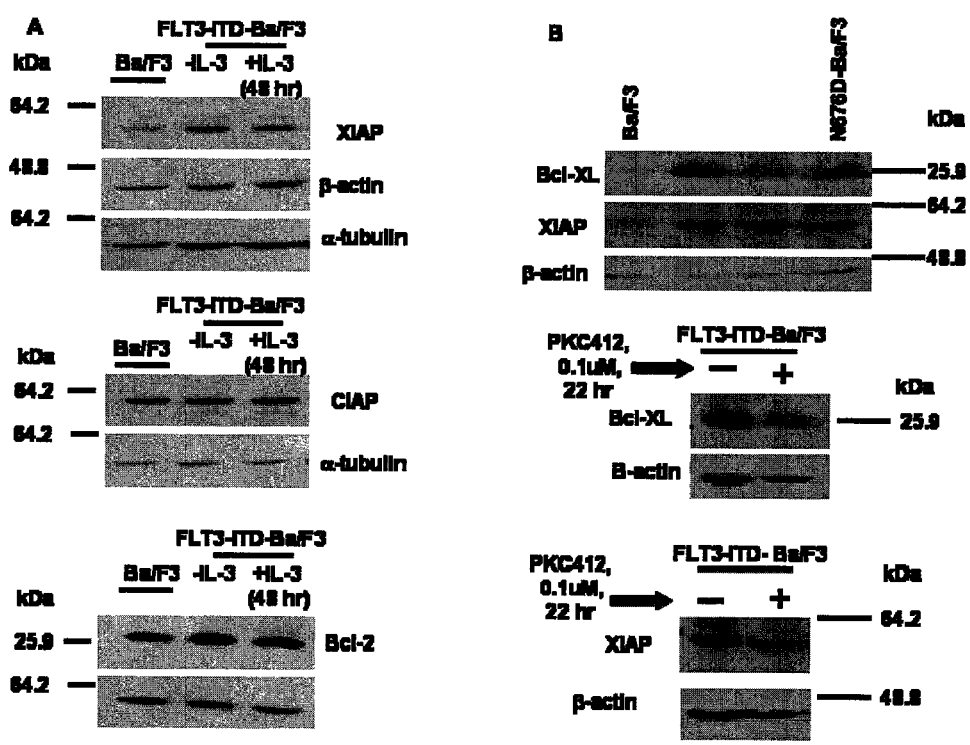
FIG. 10 illustrates immunoblots showing XIAP, CIAP, Bcl-2, and Bcl-XL expression in mutant FLT3-Ba/F3 cells versus control Ba/F3 cells. Immunoblots were hybridized with a beta-actin antibody and/or an alpha-tubulin antibody as a loading control.

The expression of a panel of anti-apoptotic signaling factors, including IAP substrates of N-[1-cyclohexyl-2-oxo-2-(6-phenethyl-octahydro-pyrrolo[2,3-c]pyridin-1-yl-ethyl]-2-methylamino-propionamide (LBW242), and Bcl-2 and BclxL, is studied in mutant FLT3-expressing cells. Only modest fluctuations in XIAP, Bcl-2, and BclxL protein expression in FLT3-ITD-expressing Ba/F3 cells are observed, as compared to parental Ba/F3 cells, with no detectable change in CIAP1 expression, and no effect of IL-3 on protein levels following 2 days of exposure of cells to growth factor, see FIG. 10. Treatment of FLT3-ITD-Ba/F3 cells with 0.1 µM PKC412 for 22 hours led to a partial decrease in BclxL and XIAP protein expression, suggesting that FLT3 regulates expression of these proteins, see FIG. 10.

EXAMPLE 12

Cell Viability and Apoptosis Analysis

The trypan blue exclusion assay has been previously described [see Weisberg et al. (2002)], and was used to determine proliferation of cells cultured in the presence and absence of PKC412 and (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide. Cell viability is reported as percentage of control (untreated) cells. Error bars represent the standard error of the mean for each data point. Apoptosis of drug-treated cells was measured using the Annexin-V-Fluos Staining Kit (Boehringer Mannheim, Indianapolis, Ind.), as previously described. See Weisberg et al. (2002).

EXAMPLE 13

Drug Combination Studies PKC412 and (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y)

For drug combination studies, PKC412 and (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) are added simultaneously at fixed ratios to FLT3-ITD-Ba/F3 cells or AML-derived MOLM13-luc+ FLT3-expressing cells. Cell viability is determined using the Trypan blue exclusion assay, and expressed as the function of growth affected (FA) drug-treated versus control cells, see FIG. 11.

EXAMPLE 14

Combination Effects of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and PKC412 Against PKC412-Sensitive Cells (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) is tested in combination with PKC412 against FLT3-ITD-Ba/F3 cells. Positive enhancement effects are observed between the two agents, see FIG. 12.

(S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and PKC412 are also tested in combination against the human acute leukemia, FLT3-ITD-expressing cell line, MOLM13-luc+, see FIG. 11 and both agents are found to enhance inhibition of cellular proliferation as compared to each drug alone only at higher doses.

EXAMPLE 15

Proliferation Studies Show Combination Effects of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and Doxorubicin or Ara-c, Against PKC412-Sensitive Mutant FLT3-Expressing Cells The combined effects between PKC412 and standard chemotherapy agents, such as doxorubicin and Ara-c, against FLT3-ITD-Ba/F3 cells show positive enhancement effects for the combination of PKC412 and doxorubicin across a range of doses (ED50-ED90), see FIGS. 13-15.

EXAMPLE 16

In Vivo Investigation of Effects of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and PKC412, Alone and Combined To directly assess the in vivo anti-tumor efficacy of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) alone, PKC412 alone, and the combination of (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and PKC412, a mouse model of acute leukemia is studied in which tumor burden is quantified by non-invasive imaging of luminescent tumor cells FIG. 16.

Murine FLT3-ITD-Ba/F3 cells are engineered to stably express firefly luciferase, and NCr nude mice are then inoculated with these cells. Non-invasive imaging is used to serially assess tumor burden, and mice with established leukemia are divided into cohorts with similar tumor burden.

PKC412, (S)-N-((S)-1-Cyclohexyl-2-{(8)-2-[4-(4-fluoro-benzoyl)-thiazol-2-yl]-pyrrolidin-1-yl}-2oxo-ethyl)-2-methylamino-propionamide or PKC412 combined with (S)-N-((S)-1-Cyclohexyl-2-{(8)-2-[4-(4-fluoro-benzoyl)-thiazol-2-yl]-pyrrolidin-1-yl}-2oxo-ethyl)-2-methylamino-propionamide (Compound Y) are then administered via oral gavage, as is the vehicle. Administration of both agents together is performed by gavaging with one agent approximately 20-30 minutes prior to gavaging with the other agent. Mice were given vehicle alone, (S)-N-((S)-1-Cyclohexyl-2-{(8)-2-[4-(4-fluoro-benzoyl)-thiazol-2-yl]-pyrrolidin-1-yl}-2oxo-ethyl)-2-methylamino-propionamide (Compound Y) (50 mg/kg), PKC412 (40 mg/kg) or a combination of both (S)-N-((S)-1-Cyclohexyl-2-{(S)-2-[4-(4-fluoro-benzoyl)-thiazol-2-yl]-pyrrolidin-1-yl}-2oxo-ethyl)-2-methylamino-propionamide (Compound Y) and PKC412, see FIG. 16. The lowest tumor burden as assessed by bioluminescence (photons/second) is observed to be in the drug combination group on day 8 post-IV injection of FLT3-ITD-Ba/F3-luc+ cells (and corresponding to 8 days of drug treatment, respectively), see FIG. 16.

The invention claimed is:

1. A method of treating a warm-blooded animal having acute myeloid leukemia (AML), comprising administering to said animal a therapeutically effective amount of (a) (S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, or a pharmaceutically salt thereof, in combination with (b) midostaurin, or a pharmaceutically salt thereof.

2. A method according to claim 1, wherein the AML is resistant to conventional chemotherapy.

3. A method according to claim 1, wherein the warm-blooded animal is a human.

4. method according to claim 3, wherein the human is a juvenile human.

5. A combination which comprises (a) (S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, or a pharmaceutically salt thereof, and midostaurin, or a pharmaceutically salt thereof.

6. A pharmaceutical composition which comprises a combination as defined in claim 5.

* * * * *